US008367321B2

(12) United States Patent
Herrmann et al.

(10) Patent No.: US 8,367,321 B2
(45) Date of Patent: Feb. 5, 2013

(54) METHOD FOR DETECTION OF PATHOGENIC ORGANISMS

(76) Inventors: Bjorn Herrmann, Uppsala (SE); Leif Kirsebom, Uppsala (SE); Pelle Stolt, Uppsala (SE)

( * ) Notice: Subject to any disclaimer, the term of this patent is extended or adjusted under 35 U.S.C. 154(b) by 2740 days.

(21) Appl. No.: 10/169,831

(22) PCT Filed: Jan. 10, 2001

(86) PCT No.: PCT/SE01/00031
§ 371 (c)(1), (2), (4) Date: Nov. 13, 2002

(87) PCT Pub. No.: WO01/51662
PCT Pub. Date: Jul. 19, 2001

(65) Prior Publication Data

US 2003/0134295 A1 Jul. 17, 2003

(30) Foreign Application Priority Data

Jan. 10, 2000 (SE) ....................................... 0000061

(51) Int. Cl.
*C12Q 1/68* (2006.01)

(52) U.S. Cl. ........................................................ 435/6.1

(58) Field of Classification Search ......................... None
See application file for complete search history.

(56) References Cited

U.S. PATENT DOCUMENTS

| | | | | |
|---|---|---|---|---|
| 5,574,145 A * | 11/1996 | Barry et al. | ................ | 536/24.32 |
| 5,776,677 A * | 7/1998 | Tsui et al. | .................... | 435/6.11 |
| 7,041,490 B1 * | 5/2006 | Griffais et al. | ............ | 435/252.3 |

FOREIGN PATENT DOCUMENTS

WO 99/11653 3/1999

OTHER PUBLICATIONS

Hermann et al. (Int. J. Systematic Evolutionary Micro, 2000, 50:149-158).*
Dahloff et al. (Appl. Environ. Micro, 2000, 66(8):3376-3380).*
James et al. (Cell, 1988, vol. 52, p. 19-26, IDS reference).*
Buck et al. (Biotechniques, 1999, 27(3):528-536).*
Herrmann et al. (J Clin Microbiol. Aug. 1996;34(8):1897-902) in view Tsui et al. (U.S. 5,776,667).*
Thomas H. Jukes et al., "Evolution of Protein Molecules," Chapt. 24 in Mammalian Protein Metabolism, ed. By H.N. Munro, V. III, 1969, pp. 21-132.
Stefan Niemann et al., "Differentiation among Members of the Mycobacterium tuberculosis Complex by Molecular and Biochemical Features: Evidence for Two Pyrazinamide-Susceptible Subtypes of *M. bovis*", Journal of Clinical Microbiology, Jan. 2000, pp. 152-157, American Society for Microbiology.
Cho, M. et al., *International Journal of Systematic Bacteriology* (1998), 48, pp. 1223-1230.
Elizabeth S. Haas et al., "Evolutionary Variation in Bacterial RNase P RNAs," Nucleic Acids Research, V. 26, 1998, pp. 4093-4099.
Bryan D. James et al., "The Secondary Structure of Ribonuclease P RNA, the Catalytic Element of a Ribonucleoprotein Enzyme," Cell, V. 52, 1988, pp. 19-26.
Abed, Y., C. Bollet, and P. De Micco 1995. Demonstration of *Mycobacterium kansasii* species heterogeneity by the amplification of the 16S-23S spacer region. J. M. Microbiol. 43: 156-158.
Alcaide F., I. Richter, C. Bernasconi , B. Springer, C. Hagenau R. Schulze-Robbecke, E. Tortoli, R. Martin, E. C. Böttger, and A. Telenti. 1997. Heterogeneity and clonality among isolates of *Mycobacterium kansasii*: Implications for epidemiological and pathogenicity studies. J. Clin. Microbiol. 35:1959-1964.
Bascunana C. R. and K. Belak K. 1996. Detection and identification of mycobacteria in formalin-fixed, paraffin-embedded tissues by nested PCR and restriction enzyme analysis. J. Clin. Microbiol. 10:2351-2355.
Brännvall, M., J. G. Mattsson, S. G. Svärd S.G., and L. A. Kirsebom. 1998. RNase P RNA structure and cleavage reflect the primary structure of tRNA genes. J. Mol. Biol. 283:771-83.
Brown J. W. and N. R. Pace. 1992. Ribonuclease P RNA and protein subunits from bacteria. Nucleic Acids Res. 20:1451-1456.
Cole S. T., R. Brosch, J. Parkhill, T. Garnier, C. Churcher, D. Harris, S. V. Gordon, K. Eiglmeier, S. Gas, C. E. 3rd Barry, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, B. G. Barrell, et al., 1998. Deciphering the biology of *Mycobacterium tuberculosis* from the complete genome sequence. Nature 393:537-44.
Crawford J. T. 1994. Development of rapid techniques for identification of *M. avium* infections. Res. Microbiol. 145:177-181.
Devallois A., M. Picardeau, K.S. Goh, C. Sola, V. Vincent, and N. Rastogi. 1996. Comparative evaluation of PCR and commercial DNA probes for detection and identification to species level of *Mycobacterium avium* and *Mycobacterium intracellulare*. J. Clin. Microbiol. 34:2756-2759.
Devallois A., M. Picardeau, C. N. Paramasivan, V. Vincent, and N. Rastogi. 1997 Molecular characterization of *Mycobacterium avium* complex isolates giving discordant results in AccuProbe tests by PCR-restriction enzyme analysis, 16S rRNA gene sequencing, and DT1-DT6 PCR. J. Clin. Microbiol. 35:2767-2772.
Frothingham R., and K.H. Wilson. 1994. Molecular phylogeny of the *Mycobacterium avium* complex demonstrates clinically meaningful divisions. J. Infect. Dis. 169:305-312.
Gardiner K. and N. R Pace. 1980. RNase P of *Bacillus subtilis* has an RNA component. J. Biol. Chem. 255:7507-7509. Guerrier-Takada, C., K. Gardiner, T. L. Marsh, N. R. Pace, and S. Altman. 1983. The RNA moiety of RNase P is the catalytic subunit of the enzyme. Cell 35:849-857.
Herrmann B., O. Winqvist, J. G. Mattsson , and L. A. Kirsebom LA. 1996. Differentiation of *Chlamydia* spp. by sequence determination and restriction endonuclease cleavage of RNase P RNA genes. J. Clin. Microbiol. 34:1897-1902.
Iinuma Y., S. Ichiyama, Y. Hasegawa, K. Shimokata, S. Kawahara, and T. Matsushima. 1997. Large-restriction-fragment analysis of *Mycobacterium kansasii* genomic DNA and its application in molecular typing. J. Clin. Microbiol. 35: 596-599.

(Continued)

*Primary Examiner* — Christopher M. Babic
(74) *Attorney, Agent, or Firm* — Young & Thompson

(57) ABSTRACT

A method for detection of pathogenic organisms wherein the method includes differentiation between species. The method is especially suitable to detect and to diagnose infection by pathogenic organisms which are hard and/or laborious to detect with conventional methods. The method relies upon analysis of specific variable regions of the RNase P RNA gene, namely the P3 and/or P19 region(s).

3 Claims, 10 Drawing Sheets

OTHER PUBLICATIONS

Ji -eY., K. E. Kempsell, M. J. Colston and R. A. Cox. 1994 Nucleotide sequences of the spacer-1, spacer-2 and trailer regions of the rrn operons and secondary structures of precursor 23S rRNAs and precursor 5S rRNAs of slow-growing mycobacteria Microbiology 140:1763-1773.
Kapur V., L.-L. Li, M. R. Hamrick, B. B. Plikaytis, T. M. Shinnick, A. Telenti, Jr W. R. Jacobs, A. Banerjee, S. Cole, K.Y. Yuen, J. E. Clarridge III, B. N.Kreiswirth, and J. M. Musser. 1995. Rapid *Mycobacterium* species assignment and unambiguous identification of mutations associated with antimicrobial resistance in *Mycobacterium tuberculosis* by automated DNA sequencing. Arch. Pathol. Lab. Med. 119:131-138.
Kole R. M. F. Baer, B. C. Stark, and S. Altman. 1980. *E. coli* RNAase P has a required RNA component in vivo. Cell 19:881-887.
Kulski J.K., C. Khinsoe, T. Pryce, and K. Christiansen. 1995. Use of a multiplex PCR to detect and identify *Mycobacterium avium* and *M. intracellulare* in blood culture fluids of AIDS patients. J. Clin. Microbiol. 33:668-674.
Nishimori K., M. Eguchi, Y. Nakaoka, Y. Onodera, T. Ito, and K. Tanaka. 1995. Distribution of IS9O1 in strains of *Mycobacterium avium* complex from swine by using IS9O1-detecting primers that discriminate between *M. avium* and *Mycobacterium intracellulare*, J. Clin. Microbiol. 8:2102-2106.
Picardeau M., G. Prod'hom, L. Raskine, M. P. LePennec, and V. Vincent. 1997. Genotypic characterization of five subspecies of *Mycobacterium kansasii*. J. Clin. Microbiol. 35 25-32.
Rastogi N., W. W. Barrow, J. O. Falkinham III, C. O. Thoen, J. T. Crawford, B. T. Mangura, L. B. Reichman, L. B Heifets, B. Dautzenberg, L. S. Young, L. E. Bermudez, C. D. Inderlied, A. E. Suzuki, J. M. Inamine, P. R. J. Gangadharam, M. V. Reddy, M. Denis, H. Shiratsuchi, J., L. Johnson, J. J. Ellner, J. T. Belisle, and P. J. Brennan. 1994. 11th Forum in Microbiology, "Laboratory and clinical aspects of the *Mycobacterium avium* epidemic: contributing factors associated with variability of drug susceptibility and immune responsiveness, and the multifaceted nature of pathogenicity". Res. Microbiol. 145:167-261.
Rastogi N., J. J. McFadden, M. L. Gourgeon, L. Montagnier, F. M. Collins, C. R. Horsburgh, R. J. Coker, T. J. Hellyer, I. N. Brown, J. N. Weber, I. M. Orme, D. Chatterjee, J. D. A. Van Embden, D. Van Soolingen, P. M. Small, P. W. M. Hermans, S. E. Hoffner, G. Källenius, S. B. Svenson, R. S. Wallis, J. J. Ellner, H. Shiratsuchi, G. A. W. Rook, A. Vyakarnam, D. M. Yajko, L. S. Young, L. E. M. Bermudez, C. B. Inderlied, Z. M. Kunze, F. Portaels, and V. Labrousse. 1992. 8th Forum in Microbiology, "Mycobacteria and AIDS: epidemiological and genetic markers, virulence factors and interactions with the immune system." Res Microbiol. 143:357-440.
Richter E. S. Niemann, S. Rusch-Gerdes, and S. Hoffner. 1999 Identification of *Mycobacterium kansasii* by using a DNA probe (AccuProbe) and molecular techniques. J. Clin. Microbiol. 37: 964-970.
Roth A., M. Fischer, M. E. Hamid, S. Michalke, W. Ludwig, and H. Mauch. 1998, Differentiation of phylogenetically related slowly growing mycobacteria based on 16S-23S rRNA gene internal transcribed spacer sequences. J. Clin. Microbiol. 36:139-147.
Siegel, R. W., A. B. Banta, E. S. Haas, J. W. Brown, and N. R. Pace. 1996. *Mycoplasma fermentans* simplifies our view of the catalytic core of ribonuclease P RNA. RNA 2: 452-62.
Snapper, S. B., R. E. Melton, S. Mustafa, T. Kieser, and Jacobs WR Jr. 1990. Isolation and characterization of efficient plasmid transformation mutants of *Mycobacterium smegmatis*. Mol. Microbiol 4:1911-1919.
Sritharan V., J.V. Iralu, and R.H. Barker Jr. 1995. Specificity of diagnostic PCR amplification for *M. avium* using the probe pMAV22. Mol. Cell. Probes 9:71-74.
Stark, B. C., R. Kole, E. J. Bowman and S. Altman. 1978. Ribonuclease P: an enzyme with an essential RNA component. Proc. Natl. Acad. Sci. USA 3717-3721.
Telenti, A. F. Marchesi, M. Balz, F. Bally E.C. Böttger, and T. Bodmer. 1993. Rapid identification of mycobacteria to the species level by polymerase chain reaction and restriction enzyme analysis. J. Clin. Microbiol. 31:175-178.
Van der Giessen J. W. B., R. M. Haring, and B. A. M. Van der Zeijst. 1994 Comparison of the 23S ribosomal RNA genes and the spacer region between the 16S and 23S rRNA genes of the closely related *Mycobacterium avium* and *Mycobacterium paratuberculosis* and the fast-growing *Mycobacterium phlei*. Microbiology. 140:1103-1108.
Vioque A. 1992. Analysis of the gene encoding the RNA subunit of ribonuclease P from cyaobacteria. Nucleic Acids Res. 20:6331-37.
Woolford A. J., R. G. Hewinson, M. Woodward, and J. W. Dale 1997. Sequence heterogeneity of an mpb70 gene analogue in *Mycobacterium kansasii*. FEMS Microbiol. Lett. 148:43-48).
Altman, S. & Kirsebom, L. A. (1999). Ribonuclease P. In the RNA world: Second edition (Gesteland, R.F., Cech, T. & Atkins, J.F., eds.), pp. 351-380. Cold Spring Harbour Laboratory Press, New York.
Amann, R., Springer, N., Schonhuber, W., Ludwig, W., Schmid, E. N., Muller, K. D., Michel R. (1997). Obligate intracellular bacterial parasites of acantharnoebae related to *Chlamydia* spp. *Appl Environ Microbiol* 63, 115-121.
Andersen, A. A. & Van Deusen, R. A. (1988). Production and partial characterization of monoclonal antibodies to four *Chlamydia psittaci* isolates. *Infect Immun* 56, 2075-2079.
Baker, J. A. (1942). A virus obtained from a pneumonia of cats and its possible relation to the cause of atypical pneumonia in man. *Science* 96, 475-476.
Black, C. M., Tharpe, J. A. & Russell, H. (1992). Distinguishing *Chlamydia* species by restriction analysis of the major outer membrane protein gene. *Mol Cell Probes* 6, 395-400.
Brown, J. W., Nolan, J. M., Haas, E. S., Rubio, M-A. T., Major, F., Pace, N. (1996). Comparative analysis of ribonuclease P RNA using gene sequences from natural microbial populations reveals tertiary structural elements. *Proc Natl Acad Sci* 93, 301-3006.
Brown, J. W. (1998). The Ribonuclease P Database. *Nucl Acids Res* 26, 351-352.
Chirgwin, K., Roblin, P. M. & Hammerschlag, M. R. (1989). In vitro susceptibilities of *Chlamydia pneumoniae* (*Chlamydia* sp. strain TWAR). *Antimicrob Agents Chemother* 33, 1634-1635.
Everett, K. D. & Andersen, A. A. (1997). The ribosomal intergenic spacer and domain I of the 23S rRNA gene are phylogenetic markers for *Chlamydia* spp. *Int J Syst Bacteriol*, 47, 461-473.
Everett, K. D. E., Bush R. M. & Andersen, A. A. (1999). Emended description of the order *Chlamycliales*, proposal of *Parachlamydiaceae* fam. nov. and *Simkaniaceae* fam. nov. each containing one monotypic genus, revised taxonomy of the family *Chlamydiaceae* including a new genus and five new species, and standards for the identification of organisms. *Int J Syst Bacteriol* 49, 415-440.
Francis, T., Jr., & Magill, T. P. (1938). An unidentified virus producing acute meningitis and pneumonia in experimental animals. *J Exp Med* 68, 147-160.
Fukushi, H. & Hirai, K. (1989). Genetic diversity of avian and mammalian *Chlamydia psittaci* strains and relation to host origin. *J Bacteriol* 171, 2850-2855.
Golub, O. J. & Wagner, J. C. (1947). Studies on the interference phenomenon with certain members of the psittacosis-lymphogranuloma group of viruses. *J Immunol*, 59, 59-70.
Grayston, J. T.,Kuo, C.-C.,Campbell, L. A. & Wang, S. P. (1989). *Chlamydia pneumoniae* sp nov for *Chlamydia* sp strain TWAR. *Int J Syst Bacteriol*, 39, 88-90.
Haas, E. S., Brown, J. W., Pitulle, C. & Pace, N. R. (1994). Further perspective on the catalytic core and secondary structure of ribonuclease P RNA. *Proc Natl Acad Sci* 91, 2527-2531.
Haas, E. S., Banta, A. B., Harris, J. K., Pace, N. R. & Brown, J. W. (1996). Structure and evolution of ribonuclease P RNA in Gram-positive bacteria. *Nucl Acids Res* 24, 4775-4782.
Hardt, W-D., Schlegl, J., Erdmann, V. A. & Hartmann, R. K. (1995). Kinetics and thermodynamics of the RNase P RNA cleavage reaction: Analysis of tRNA 3'-end variants. *J Mol Biol* 247, 161-172.
Hartmann, R. K. & Erdmann, V. A. (1991). Analysis of the gene encoding the RNA subunit of ribonuclease P from *T. thermophilus* HB8. *Nucl Acids Res* 19, 5957-5964.
Illner, V. F. (1960). Zur Frage der Uebertragung des Ornithosevirus durch das Ei. *Monatsh Veterinaermed* 17, 116-117.

Kahane, S., Metzer, E. & Friedman, M. G. (1995). Evidence that the novel microorganism 'Z' may belong to a new genus in the family *Chlamydiaceae, FEMS Microbiol Lett* 126, 203-207.
Kahane, S., Greenberg, D., Friedman, M. G., Haikin, H., & Dagan, R. (1998). High prevalence of "*Simkania Z*," a novel chlamydia-like bacterium, in infants with acute bronchiolitis. *J Infect Dis* 177, 1425-1429.
Kaltenboeck, B., Kousoulas, K. G. & Storz, J. (1993). Structures of and allelic diversity and relationships among the major outer membrane protein (ompA) genes of the four chlamydial species. *J Bacteriol*, 175, 487-502.
Kirsebom & Svärd (1992). The kinetics and specificity of cleavage by RNase P is mainly dependent on the structure of the amino acid acceptor stem. *Nucl Acids Res* 20, 425-432.
Kirsebom, L. A. & Svärd, S. G. (1994). Base pairing between *Escherichia coli* RNase P RNA and its substrate. *EMBO J* 13, 4870-4876.
Lieberman, D., Kahane, S., Lieberman, D., & Friedman, M.G. (1997). Pneumonia with serological evidence of acute infection with the chlamydia-like microorganism "Z". *Am. J. Respir. Crit. Care. Med.* 156, 578-82.).
Massire, C., Jaeger, L. & Westhof, E. (1998). Derivation of the three-dimensional architecture of bacterial ribonuclease P RNAs from comparative sequence analysis. *J Mol Biol* 279, 773-793.
McNutt, S. H. & Waller, E. F. (1940). Sporadic bovine encephalomyelitis (Buss disease). *Cornell Vet* 30, 437-448.
Murray, E. S. (1964). Guinea pig inclusion conjunctivitis virus. I. Isolation and identification as a member of the psittacosis-lymphogranuloma-trachoma group. *J Infect Dis* 114, 1-12.
Nigg, C. (1942). Unidentified virus which produces pneumonia and systemic infection in mice. *Science* 95 49-50.
Page, L. A. (1959). Experimental ornithosis in turkeys. *Avian Dis.*, 3, 51-66.
Palys, T., Nakamura, L. K. & Cohan, F. M. (1997). Discovery and classification of ecological diversity in the bacterial world: the role of DNA sequence data. *Int J Syst Bacteriol*47, 1145-1156.
Perez-Martinez, J. A. & Storz, J. (1985). Antigenic diversity of *Chlamydia psittaci* of mammalian origin determined by microimmunofluorescence. *Infect Immun* 50, 905-910.
Pettersson, B., Andersson, A., Leitner, T., Olzvik, O., Uhlén, M., Storey, C., Black, C. M. (1997). Evolutionary relationships among members of the genus *Chlamydia* based on 16S ribosomal DNA analysis. *J Bacterial* 179, 4195-4205.
Pudjiatmoko, Fukushi, H., Ochiai, Y., Yamaguchi, T. & Hirai, K. (1997). Phylogenetic analysis of the genus *Chlamydia* based on 16S rRNA gene sequences. *Int J Syst Bacteriol* 47, 425-431.
Richmond S. J., Sterling, P., Ashley, C. R. (1982). Virus infecting the reticulate bodies of an avian strain of *Chlamydia psittaci. FEMS Microbiol. Letters*, 14, 31-36.
Rogers, D. G., Andersen, A. A., Hogg, A., Nielsen, D.L. & Huebert, M.A. (1993). Conjunctivitis and keratoconjunctivitis associated with chlamydiae in swine. *J Am Vet Med Assoc* 203, 1321-1323.
Rodolakis, A., Bernard, F. & Lantier, F. (1989). Mouse models for evaluation of virulence of *Chlamydia psittaci* isolated from ruminants. *Res Vet Sci* 46, 34-39.
Saitou, N. & Nei, M. (1987). The neighbor-joining method: a new method for reconstructing phylogenetic trees. *Mol Biol Evol* 4, 406-425.
Schachter, J. & Meyer, K. F. (1969). Lymphogranuloma venereum. II. Characterization of some recently isolated strains. *J Bacteriol* 99, 636-638.
Spalatin, J., Fraser, C. E. O., Connell, R. P. & Berman, D. T. (1966). Agents of psittacosis-lymphogranulomavenereum group isolated from muskrats and snowshoe hares in Saskatchewan. *Can J Comp Med Vet Sci* 30, 225-420.
Vioque, A. (1997). The RNase P RNA from cyanobacteria: short tandemly repeated repetitive (STRR) sequences are present within the RNase P RNA gene in heterocyst-forming cyanobacteria. *Nucl Acids Res* 25, 3471-3477.
Wang, S.-P. & Grayston, J. T. (1962). Classification of trachoma virus strains by protection of mice from toxic death. *J Immunol* 90, 849-856.
Wills, J. M., Gruffydd-Jones, T. J., Jones T, Richmond, S., Paul, I. D. (1984). Isolation of *Chlamydia psittaci* from cases of conjunctivitis in a colony of cats. *Vet Rec* 114, 344-346.
Zhang, Y. X., Fox, J. G., Ho, Y., Zhang, L., Stills, H. J. & Smith, T. F. (1993). Comparison of the major outer-membrane protein (MOMP) gene of mouse pneumonitis (MoPn) and hamster SFPD strains of *Chlamydia trachomatis* with other *Chlamydia* strains. *Mol Biol Evol* 10, 1327-42.

* cited by examiner

Fig. 1

```
M. cel    -----------------------------***************-T---G**************G--------
M. xen    -----------------------------T-CCT***********GG--CGC-*--AC--**-G---------
M. mal    --------------------------------CC***********GG--GA--*--*C-G-T-C---------
M. lep    ----C-------------------------T--C***********GG--TGA-A--CC-G-TAA---------
M. for    ---------------------------A-CG--GC***********-AA-CG**************-G-----
M. sme    ---------------------------ATC*****************GC-TG**************AT-----
M. avi    ------------------------------T***************--C-***************--------
M. par    ------------------------------T***************--C-***************--------
M. gor    ---------------------------C--A--C--T-***********-GA--*---G-C-AC-T-------
M. mar    ------------------------------G--T-----C----T-**------**--------C---A----
M. int    --------------------------GC--******************--G-A-*--********--GT----
M. gas    ------------------------------A--C--***********---G-A-*--AC-G---C--------
M. kan    ------------------------------A--T--***********---G-A-*--A--G---C----C---
M. mic    ------------------------------------------------------*------------------
M. bov    ------------------------------------------------------*------------------
M. tb     CGGATGAGTTGGCTGGGCGGCCGCGGCTCGCGTAGGGCTTGTGTGGATTCACGA*GGTTCAGCGTCGAGTCGA

M. cel    -----------------------------G-------------C---G------C------------------
M. xen    -----------------------------G--------A----C---G------C------------------
M. mal    -------------------------------------------------------------------------
M. lep    --------------------------------------A-----------------------T----------
M. for    -----------------------G-------------------------------------------------
M. sme    -------------------------------------------------------------------------
M. avi    -------------------------------------------------------------------------
M. par    -------------------------------------------------------------------------
M. gor    -------------------------------------------------------------------------
M. mar    -----------------------T--------------A----------------------------------
M. int    -------------------------------------------------------------------------
M. gas    -------------------------------------------------------------------------
M. kan    -------------------------------------------------------------------------
M. mic    -------------------------------------------------------------------------
M. bov    -------------------------------------------------------------------------
M. tb     GGAAAGTCCGGACTTCACAGAGCAGGGTGATTGCTAACGGCAATCCGAGGTGACTCGCGGGAAAGTGCCACAG

M. cel    --------------C-T---C-----T----------------------------------------------
M. xen    --------------C-T---C-----T-----------------------------------C----------
M. mal    ------A-------C-T---C-----T----------------------------------------------
M. lep    ------A-------------C-----T-----------------------------------C----------
M. for    --------------*****-AAA---T----------------------------------CC----------
M. sme    --------------*****-AAA---T----------------------------------CC----------
M. avi    --------------C-----C-----T----------------------------------CC----------
M. par    --------------C-----C-----T----------------------------------CC----------
M. gor    --------------C--GT-------T-----------------------------------C----------
M. mar    --------------C-----C-----T----------------------------------CC----------
M. int    --------------C-----C-----T-----------------------------------C----------
M. gas    ------A-------C-----C-----T-----------------------------------C----------
M. kan    ------A-------------------T-----------------------------------C----------
M. mic    -------------------------------------------------------------------------
M. bov    -------------------------------------------------------------------------
M. tb     AAAACAGACCGCCATCCTCGTGGTGGCAAGGGTGAAACGGTGCGGTAAGAGCGCACCAGCATTCCGGGTGACC
```

Fig. 1 cont.

```
M. cel    --AA-----C-------------------------------A-------TT*CG------T----------TC
M. xen    ---A-------------------------------------A-------C***G------T------------
M. mal    --AA-----C--------------------------------------**-----------------------
M. lep    ---A-----T--T--------------------T---------T---TAC*--------------------T-
M. for    -----------------------------------------A-----A-CT*GGT-----T-----------C
M. sme    -----------------------------------------------A-T-CGGT-----------------C
M. avi    ---------C--------------------------------T--TG--GCCGG*CA--------------TC
M. par    ---------C-----------------------------------TG--GC*CG-CA--------------TC
M. gor    -------------------------------------------------*------------------A--T-
M. mar    ---------------------------------T-----------T---GT-GG-----------------T-
M. int    ---------C---------------------------------------GCT*G-----------------T-
M. gas    -------------------------------------------------*---G--------------A--A-
M. kan    -------------------------------------------------*---G--------------A---C
M. mic    -------------------------------------------------*-----------------------
M. bov    -------------------------------------------------*-----------------------
M. tb     GGGGTGGCTAGGCAAACCCCACCCGAAGCAAGGCCAAGAAGGCCGCACC*GAAAGTGCGGCCGCGCAGGCGCT

M. cel    C-----------------------------------T------------G-----------------------
M. xen    ------------------------------------T------------G-----------------------
M. mal    C-----------------------------------T-----------CG-----------------------
M. lep    C---A-C-----------------------------T-----------C------------------------
M. for    ------C-----------------------------T-----------CG-----------------------
M. sme    C-----------------------------------T----T------CG---GC-AC---------------
M. avi    C------------------------------------------------G-----------------------
M. par    C------------------------------------------------G-----------------------
M. gor    ------C------------T----------------------------C------------------------
M. mar    ------C------------T---------------------T------C---------C--------------
M. int    C-----C------------------------------------------G-----------------------
M. gas    C------------------T----------------T------------G-----------------------
M. kan    G------------------T-----------------------------G-----------------------
M. mic    -------------------------------------------------------------------------
M. bov    -------------------------------------------------------------------------
M. tb     TGAGGGTTGCTCGCCCGAGCCTGCGGGTAGGCCGCTCGAGGCACCCGGTAACGGTGTGTCCAGATGGATGGTC

M. cel    -------C--A*********---******--T-------T------------------------A
M. xen    ------CC--T----C-*-TTCGC*****--T----G---------------------------A
M. mal    -------C---------*GCT-AT--C-C-------G---------------------------A
M. lep    -------C---A----A*G--AAT--C-C-TT----G------------------T--------T
M. for    ---A---GC-----****C-G-AACG***--A--GC---C------------------------A
M. sme    ------CCA-----****--AGAT*****-------G---------------------------A
M. avi    -------C-------G-****--TC-***-----------------------------------A
M. par    -------C-G-----G-****--TC-***-----------------------------------A
M. gor    -T--------------GG-TTAAA--C-C-----T-G-------------------G-------A
M. mar    -------C-------C-*G-T-CA--C-C-----T-T-------------------G-------A
M. int    -------CA--------*GCT*CACGC-C-----T-G---------------------------*
M. gas    -----------------*G-T-CA--C-C------AG---------------------------A
M. kan    -----------------*G-T-CA--C-C------AG---------------------------A
M. mic    -----------------*----------------------------------------------A
M. bov    -----------------*----------------------------------------------A
M. tb     GCCGCCGTGCCGCCGTT*AGCTTGGCTGTGGCGGCGCGGAACAGAATCCGGCTTACAGGCCAACT
```

Fig. 3

```
M. gastri  ---------------------------------C-------------C---------T---
67         ------------------------------G--------------------------T---
69         ------------------------------G--------------------------T---
56         ---------------------------------------------------------T---
fzb        -------------------------------------------------------------
2721       ---------------------------------------------------------T---
12748      CGGATGAGTTGGCTGGGCGGCCGCGGCTCGAGTTGGTTCGCAAGGATCGGCGCCGAGCCGA

M. gastri  -------------------------------------------------------------
67         ---------------------------------------------------A---------
69         ---------------------------------------------------A---------
56         ---------------------------------------------------A---------
fzb        -------------------------------------------------------------
2721       ---------------------------------------------------A---------
12748      GGAAAGTCCGGACTTCACAGAGCAGGGTGATTGCTAACGGCAATCCGAGGTGACTCGCGGG

M. gastri  --------------------------C-----C----------------------------
67         --------------------------------C----------------------------
69         --------------------------------C----------------------------
56         --------------------------------C----------------------------
fzb        -------------------------------------------------------------
2721       --------------------------------C----------------------------
12748      AAAGTGCCACAGAAAACAAACCGCCATCCTCGTGGTGGTAAGGGTGAAACGGTGCGGTAAG

M. gastri  -------------------------------------------------------------
67         -------------------------------------------------------------
69         -------------------------------------------------------------
56         -------------------------------------------------------------
fzb        -------------------------------------------------------------
2721       -------------------------------------------------------------
12748      AGCGCACCAGCATCCCGGGTGACCGGGGTGGCTAGGCAAACCCCACCCGAAGCAAGGCCAA

M. gastri  --------------------------------ATC--------------------------
67         -----------C---------------------TC--------------------------
69         -----------C---------------------TC--------------------------
56         -----------C---------------------TC--------------------------
fzb        ---------------------G--G------------------------------------
2721       -----------C---------------------TC--------------------------
12748      GAAGGCCGCACGAAGGTGCGGCCGCGCAGACGCCGGAGGGTTGCTCGCCCGAGTCTGCGGG

M. gastri  ---------T---------------------------------------------------
67         ---------T---------------------------------------------------
69         ---------T---------------------------------------------------
56         ---------T---------------------------------------------------
fzb        -------------------------------------------------------------
2721       ---------T---------------------------------------------------
12748      TAGGCCGCTCGAGGCACCCGGTGACGGTGTGTCCAGATGGATGGTCGCCGCCGTGCCGCCG

M. gastri  -------------------------------------------------
67         -------------------------------------------------
69         -------------------------------------------------
56         -------------------------------------------------
fzb        -------------------------------------------------
2721       -------------------------------------------------
12748      TTGGTTCAGCCGCGGCGGCAGGGAACAGAATCCGGCTTACAGGCCAACA
```

METHOD FOR DETECTION OF PATHOGENIC ORGANISMS

FIELD OF THE INVENTION

The present invention relates to a method for detection of pathogenic organisms wherein the method includes differentiation between species. The method is especially suitable to detect and to diagnose infection by pathogenic organisms which are hard and/or laborious to detect with conventional methods. The method relies upon analysis of specific variable regions of the RNase P RNA gene.

BACKGROUND OF THE INVENTION

RNase P is an enzyme present in all living cells. It catalyses the removal of 5' leader sequences from tRNA precursor molecules. In bacteria, RNase P consists of an RNA molecule of some 400 nt in length (11, 28) and a small (about 120 aa) protein (33). In the division bacteria, the RNA moiety has been shown to function as an efficient catalyst in vitro (12); hence at least in these organisms, RNase P is a ribozyme (an RNA molecule catalysing chemical reactions). Bacterial RNase P RNAs have been separated into two main structural classes. Type A is the most common structural class and type B is found in the low G+C Gram-positive Bacteria (50). The secondary structure of RNase P RNA has been characterised for many bacterial lineages and variation among the helices provides useful phylogenetic information (51).

The RNase P RNA gene sequences are not very well preserved between bacterial groups, (5) but within a genus, genes can be quite similar. Several hundreds of RNase P RNA sequences are present in the RNase P RNA database ((http://jwbrown.mbio.ncsu.edu/RNaseP/home.html).

The order Chlamydiales is a group of obligately intracellular bacteria which have a unique developmental cycle and pathogenicity. They are parasites of humans and a wide variety of animals. Species in the Chlamydiaceae family have recently been reclassified into two genera, *Chlamydia* and *Chlamydophila*, that include nine species (43). In addition, new families now also belong to Chlamydiales, and they include Parachlamydiaceae and Simkaniaceae (43). The type species of Parachlamydiaceae is *Parachlamydia acanthamoebae*, a symbiont of the amoebae *Acanthamoeba castellani* and an occasional pathogen of people who acquire this amoebae (34). *Simkania negevensis* is the type species of Simkaniaceae and, like many other chlamydiae, also causes human infection (56, 57, 61).

It has previously been shown that the RNase P RNA genes in the genus *Clamydia* differ sufficiently between species to be useful as a diagnostic tool (13); thus the gene is potentially useful for strain differentiation. The differences between sequences also give hints to which parts of the molecule are important for catalytic activity, complementing mutational and structural studies.

Another important family of pathogens, where fast and sensitive diagnostic methods are vital, are the mycobacteria. Traditional diagnostic methods have relied on the demonstration of acid-fast bacilli in clinical samples following cultivation. This is reliable but time consuming, since slow-growing species such as *Mycobacterium tuberculosis* may need six to eight weeks to form a sufficiently large population. In the last few years, many PCR-based detection assays have been developed based on eg the hsp60 gene (16) or the variable interspersing region between the 16S and 23S rRNA genes (15, 24, 30) and this trend continues.

The RNase P RNA gene sequence from *M. tuberculosis* is known (6) as well as that from *M. bovis* BCG and *M. leprae*. The *M. bovis* sequence is identical to that from *M. tuberculosis*, while there are differences to *M. leprae*. The regions in the RNase P RNA gene which have been indicated by other means as important for catalytic activity, were almost totally conserved between the mycobacteria. The close relationship within microbial genuses, such as mycobacteria, has rendered differentiation between species of the same genus very difficult or impossible.

SUMMARY OF THE INVENTION

The present invention solves the problem of differentiation between species within the same genus, such as mycobacteria and chlamydia. Furthermore, the present invention solves the problem of detecting pathogens which are hard and/or laborious to detect with conventional methods.

The inventive method may in principle be used for diagnosing infection by any kind of pathogenic organism.

Thus the pathogens include archaebacteria and eubacteria. The latter contains as its principal groups gliding bacteria, spirochetes, rigid bacteria and mycoplasmas. Rigid bacteria include actinomycetes and simple unicellular bacteria. The latter group consists of obligate intracellular parasites and free-living bacteria. Among the free-living, variants there are (1) gram-positive bacteria in which group there are (a) cocci, (b) non-sporulating rods, (c) sporulating rods that can be further subdivided into obligate aerobes and obligate anaerobes; and (2) gram-negative bacteria in which there are (a) cocci, (b) non-enteric rods with spiral forms and straight rods, and (c) enteric rods with facultative anaerobes, obligate aerobes and obligate anaerobes. For specific bacteria species see further Medical Microbiology, (Brooks et al, eds., 19th ed. (1991), Prentice-Hall International, USA).

The pathogens include also fungi, including pathogenic yeasts and molds. Examples are *Apergillus, Candida, Absidia, Mucor, Phizopus, Cryptococcus, Hisoplasma, Blastomyces, Coccidiodes, Paracoccidiodes, Sporotrichosis, Chromoblastomycosis, Mycetoma, Microsporum, Trichophyton* and *Epidermophyton.*

Other pathogens that may be diagnosed may be found among the protozoa and algae.

Of course, the method of the invention can also be used for detection of non-pathogenic bacteria.

The following bacteria are especially interesting for the purposes of the present invention: Bacteria of phylum II—Green bacteria; Phylum III—Deinobacteria (Thermus/Deinococcus); Phylum IV—Spirochetes; Phylum VI—Gram negative anaerobes and gliding bacteria (Bacteroides/Flavobacterium); Phylum VIII—*Chlamydia*; Phylum IX—Gram positives with the three lineages: lineage A ("Gram negatives"), lineage B (G+C-rich bacteria), lineage C (G+C-poor bacteria); Phylum X—cyanobacteria; Phylum XI—proteobacteria with the five lineages alpha, beta, gamma, delta and "E".

The present inventors detected differences in the RNase P RNA gene which were sufficient to enable species determination.

In a first aspect, the invention relates to a method for detection of pathogenic organisms including inter-species differentiation, comprising using the P3 and/or P19 hypervariable region(s) of the RNase P RNA gene as a diagnostic target.

The purpose of the method of the invention may be, for example, diagnose of infection caused by pathogenic bacteria and epidemic investigation of the spreading of drug resistant bacteria.

Preferably, the region(s) is/are amplified, such as by PCR (Polymerase Chain reaction) and sequenced or otherwise fingerprinted for species identification, such as by heteroduplex analysis, size determination, RFLP (Restriction Fragment Length Polymorphism), melting point determination etc.

In a second aspect the invention relates to a method for detection of bacteria including inter-species differentiation, comprising amplification of nucleic acids of hypervariable region(s) of the RNase P RNA gene from the pathogens; forming a heteroduplex with related nucleic acid; and analysis thereof.

An example of a method according to the invention involving a heteroduplex analysis, comprises of an amplification reaction, a hybridisation step and a non-denaturing gel electrophoresis analysis. The whole process can be carried out in less than 24 hours.

In a third aspect, the invention relates to use of the P3 and/or P19 variable regions(s) in the RNAse P RNA gene as a drug target in the production of a medicament for the treatment of microbial infection.

BRIEF DESCRIPTION OF THE DRAWINGS

FIG. 1 depicts the sequence alignment of the RNase P RNA genes from mycobacteria;

FIG. 3 depicts the sequence alignment of the RNase P RNA gene from *M. gastri* (identical sequence from two different strains) and six strains of *M. kansasii*;

DETAILED DESCRIPTION OF THE INVENTION

Figure 2:
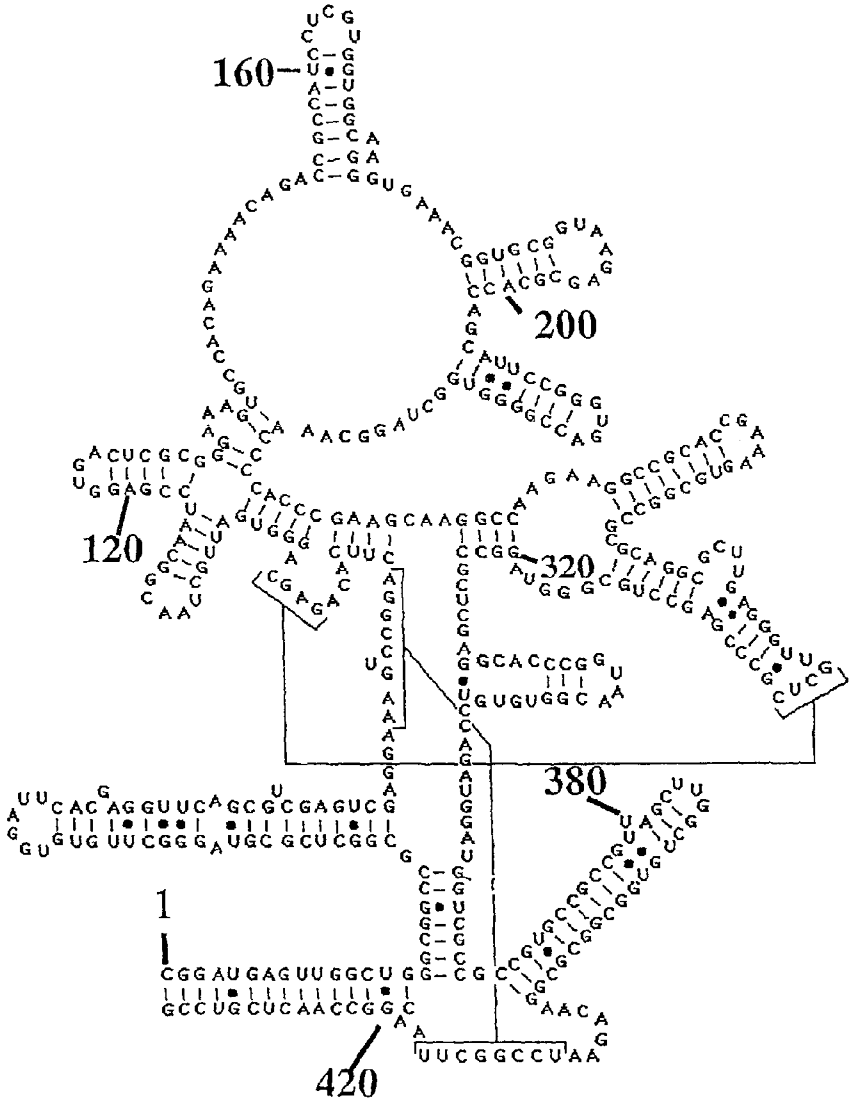
FIG. 2 depicts the secondary structure of *M. tuberculosis* RNase P RNA.

The invention will now be described in greater detail in relation to two non-limiting examples.

Example 1

*Mycobacteria*

Materials and Methods

Bacterial Strains

*Mycobacteria* used in this study are listed in Table 1 below. Clinical strains were already typed by 16S RNA gene sequencing in their respective institutes of provenance.

The RNase P RNA sequences for *M. tuberculosis, M. bovis* BCG and *M. leprae* were retrieved from the GenBank sequence database.

TABLE 1

| Species | Strain description | Provenance |
|---|---|---|
| *M. gastri* | ATCC 15754 | ATCC |
| *M. kansasii* | ATCC 12748 | ATCC |
| *M. intracellulare* | D673 | Trudeau Mycobacterial Collection |
| *M. xenopi* | ATCC 19276 | ATCC |
| *M. smegmatis* | $mc^2$ 155 | Ref. 26 |
| *M. avium* | D702 | Trudeau Mycobacterial Collection |
| *M. marinum* | clinical strain | Research Centre Borstel |
| *M. fortuitum* | clinical strain | Research Centre Borstel |
| *M. malmoense* | clinical strain | Research Centre Borstel |
| *M. paratuberculosis* | 6783 | G-F Gerlach School of Veterinary Medicine, Hanover Germany |
| *M. gordoniae* | clinical strain | Research Centre Borstel |
| *M. celatum* | clinical strain | Research Centre Borstel |

PCR Amplification of the RNase P RNA Genes

Based on the published sequences of *M. tuberculosis* and *M. leprae*, (GenBank Accession Numbers Z70692 and L78818 respectively) a primer pair was designed which hybridised close to the ends of the gene. The forward primer tbf (5' CGGATGAGTTGGCTGGGCGG 3') and reverse primer tbr (5' GTTGGCCTGTAAGCCGGATT 3') both show one mismatch to the *M. leprae* sequence. Using this primer pair, the RNase P gene could be amplified from all mycobacteria tested. Most reactions were run on untreated mycobacteria from cultures, without previous isolation and purification of chromosomal DNA. PCR was done in 50 μl reactions in a Rapidcycler capillary PCR apparatus (Idaho technology, Idaho Falls USA) with the following parameters: 94° C. 10"; 50° C. 10"72° C. 15".

Sequencing

PCR products were purified over 1 percent agarose gels to remove the primers. Approximately 1/20 of the purified DNA was used for automated sequencing with the same primers as were used in the amplification reaction. Sequencing was done on an Applied Biosystems model 310 capillary sequencer.

Heteroduplex Analysis

For heteroduplex analysis of the RNase P P3 loop region, DNA was amplified (50 μl reactions) with the oligonucleotides tbf and 280r (5' CTTGCTTGCCCTCCCTTTGCC 3') which give a product of about 250 bp. The products were gel purified and approximately 1/10 of the products used in each analysis. DNA was mixed with equal amounts of DNA from *M. tuberculosis*, heated to 95° C. for 1' and allowed to cool to room temperature. The products were separated on 10 percent non-denaturing polyacrlamide gels run at 15 mA for 14 hrs. Bands were visualised by silver staining.

Silver Staining of DNA Gels

Gels were fixated in 10 percent ethanol for 5', and incubated in 1 percent nitric acid for 5'. Staining was in a 1 mg/ml solution of silver nitrate for 30'. Bands were developed in a sodium carbonate/formaldehyde solution (15 g anhydrous sodium carbonate and 300 μl 37 percent formaldehyde in 500 ml water) until clearly visible. The reaction was stopped with 10 percent acetic acid.

Results

The results from Example 1 will be presented below in association with the accompanying drawings, FIGS. 1-5:

FIG. 1. Sequence alignment of the RNase P RNA genes from miycobacteria. Dashes indicate sequence identities; stars mark bases missing in a sequence.

FIG. 2. Secondary structure of *M. tuberculosis* RNase P RNA. Regions diverging between mycobacterial species are shaded. Minor variable regions are not shown.

FIG. 3. Sequence alignment of the RNase P RNA gene from *M. gastri* (identical sequence from two different strains) and six strains of *M. kansasii*. Bases unique to the *M. gastri* sequence are boldfaced.

Figure 4A:
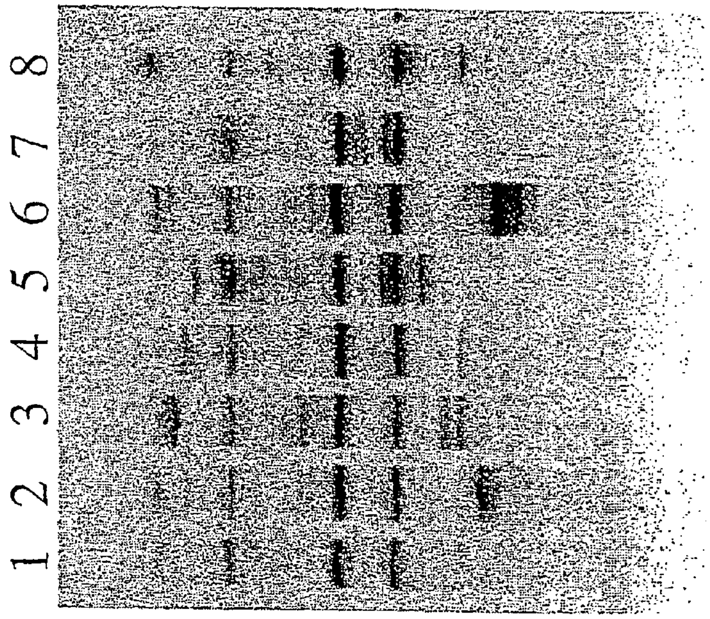
FIG. 4A depicts the Heteroduplex analysis of the first 280 bp from RNase P RNA gene regions from different mycobacteria.

FIG. 4A. Heteroduplex analysis of the first 280 bp from RNase P RNA gene regions from different mycobacteria. DNA from diverse mycobacterial species was hybridised with *M. tuberculosis* DNA and the resulting duplexes separated on a 10 percent polyacrylamide gel. Lane 1, control DNA from *M. tuberculosis*; lane 2, *M. avium*; lane 3, *M. intracellulare*; lane 4, *M. malmoense*; lane 5, *M. celatum*; lane 6, *M. kansasii*; lane 7, *M. vaccae*; lane 8, *M. xenopii.*

Figure 4B:
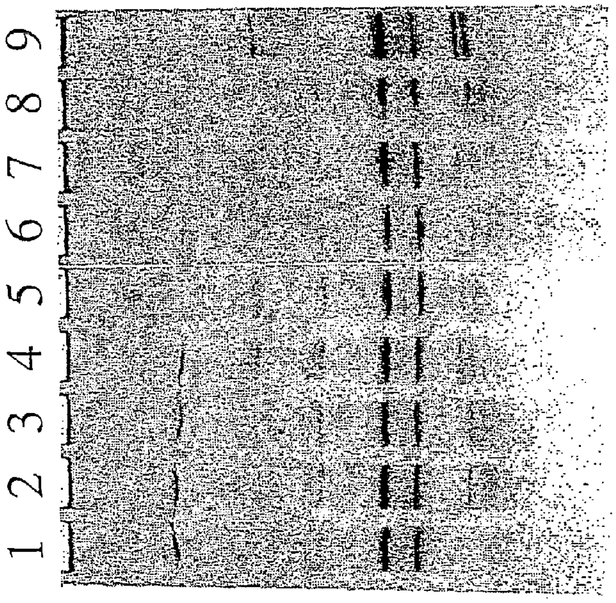
FIG. 4B depicts the Heteroduplex analysis of DNA amplified from clinical samples of bacteria believed to be either *M. intracellulare* or *M. avium*.

FIG. 4B. Heteroduplex analysis of DNA amplified from clinical samples of bacteria believed to be either *M. intracellulare* or *M. avium*. Lane 1, control DNA from *M. tuberculosis*; lanes 2, 3, 6, DNA from suspected *M. avium*; lanes 4, 5, 7, DNA from suspected *M. intracellulare*; lane 8, control DNA from *M. avium*; lane 9, control DNA from *M. intracellulare.*

Figure 5:
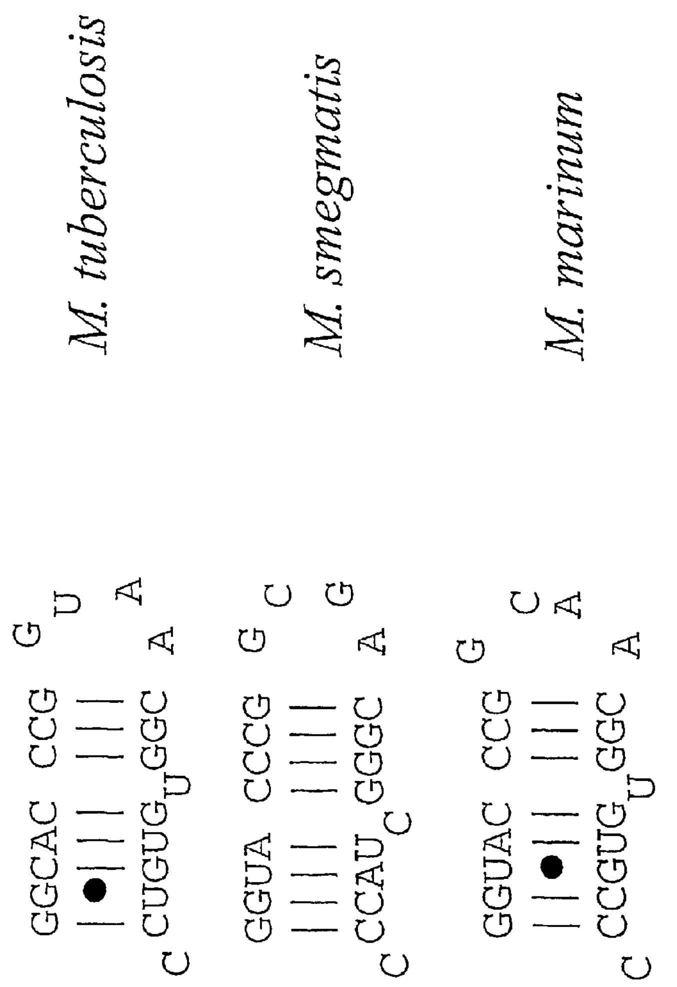
FIG. 5 depicts the suggested structure for the P18 loop of RNase P from mycobacteria, based on sequence variations within the genus.

FIG. 5. Suggested structure for the P18 loop of RNase P from mycobacteria, based on sequence variations within the genus. The sequences are from A) *M. tuberculosis*; B) *M. smegmatis*; C) *M. marinum*

In PCR amplifications of the RNase P RNA gene from mycobacteria using the oligonucleotides tbf and tbr, each reaction yielded a single fragment in the range of 387 (*M. celatum*) to 428 (*M. tuberculosis*) bp depending on mycobacterial species.

Using these oligonucleotides it was possible to amplify the RNase P RNA genes from all mycobacteria tested, using untreated cells from culture or plates. No previous purification of chromosomal DNA was necessary.

An alignment of the sequences (FIG. 1) shows very well conserved nucleotide sequences along most of the gene, with the exception of three major regions where the similarities break down and no adequate alignment is possible. The overall similarity of the genes was between 80 and 85 percent. This is not a very informative figure however, since the similarity within the well conserved regions is close to 100 percent, while the divergent regions are too dissimilar to be aligned at all.

If the divergent regions are localised on a two-dimensional representation of the RNase P RNA molecule (FIG. 2), it is conspicuous how most of the differences fall into regions which belong to ends of stem-loop structures. The major divergent regions are the P3, P16 and P19 loops. In addition, there is a deletion in the P12 loop in *M. smegmatis* and *M. fortuitum*, comprising several unpaired nucleotides of this loop. The major interspecies differences are within the P3 and P19 loops.

All species analysed had specific RNase P RNA gene sequences. Several closely related species could be differentiated on basis of the RNase P RNA sequences. The members of the MAI complex *M. avium* and *M. intracellulare* differed in several positions, including a deletion in the P19 loop in *M. avium* (FIG. 2). The very closely related (subspecies) *M. paratuberculosis* and *M. avium* were indistinguishable on basis of RNase P RNA gene sequences.

As far as our analysis went, within a species, sequences are identical. We sequenced clinical samples from all members of the *M. tuberculosis* complex (*M. tuberculosis, M. bovis, M. bovis* BCG, *M. africanum, M. microti* and *M. tuberculosis* ssp asiaticum) without detecting any deviations from the published *M. tuberculosis* sequence (6). Thus, members of this group could not be differentiated on the basis of RNase P RNA gene differences.

The possibility of sequence differences between different serovars of mycobacteria was investigated for some species. In the case of *M. avium* and *M. intracellulare*, the RNase P RNA gene from five clinical isolates (animal) of *M. avium* and five *M. intracellulare* (human) was amplified and sequenced. No differences between serovars could be detected.

The one species where heterogenous RNase P RNA gene sequences were observed between different serovars was *M. kansasii* (FIG. 3). The differences were mainly C-to-T transitions. Two strains of *M. gastri* were sequenced as well, but in this species the gene sequences were identical between isolates. In four positions, all RNase P RNA gene sequences from *M. kansasii* strains differed from those of *M. gastri*. Three of these differences were C-to-T transitions, while the fourth was a C-to-A transversion.

The interspecies differences found in the P3 and P19 loops were considered to be large enough for an attempt at a simple diagnostic application through heteroduplex analysis. The hypervariable P3 region was chosen for this analysis and amplified using the tbf and 280r oligonucleotides. Each PCR reaction yielded single bands of about 250 bp. The region from *M. tuberculosis* was used as a standard and was mixed in equal amounts with the products from different species. After separating the fragments on non-denaturing polyacrylamide gels, the bands were silver stained. There were clear differences in the heteroduplex pattern between all species tested (FIG. 4A).

This analysis was taken further by applying it to clinical samples (from the Swedish Institute of Infectious Disease Control) which had or had not been previously typed. On the resulting gel (FIG. 4B) the samples in lanes 2, 3 and 6 can be attributed to *M. avium* (compare to lane 8), while samples 4, 5 and 7 seem to be *M. intracellulare* (compare to lane 9). Sequencing the RNase P RNA gene in each case confirmed the results obtained from heteroduplex analysis.

Discussion

Compared with the case of *Clamydia*, the RNase P genes from mycobacteria are better preserved between species, with overall similarities of 80-85 percent. This overall value is misleading, however, since most differences cluster in specific regions, where the variability is of a degree that makes an unambiguous alignment impossible. All mycobacterial RNase P RNAs show a P15-P17 region of the *Clamydia* and cyanobacteria type, (13, 31) which is hardly surprising given the close relatedness of the organisms.

All species studied had their own conspicuous sequence characteristics. Within a species, no differences were seen except for *M. kansasii*, a species which has on other grounds been described as heterogeneous (1, 14, 32). Even though several of the variant positions were shared between *M. kansasii* and *M. gastri*, there are enough *M. kansasii*-specific bases in the gene to enable differentiation from the closely related *M. gastri* through microsequencing or heteroduplex analysis. *M. kansasii* is an important cause of pulmonary disease resulting from non-tuberculous mycobacteria.

The combination of very well conserved regions and hypervariable sites in the RNase P RNA gene sequence enables fast typing of unknown mycobacterial samples. Oligonucleotides will hybridise with perfect or close to perfect match to conserved regions allowing for a reliable amplification of the variable parts in between.

The *M. avium* complex (MAI) which includes *M. avium* and *M. intracellulare*, is a major opportunistic infection in AIDS patients (21, 22). Differentiating between the members of this complex requires molecular methods and our heteroduplex analysis of PCR products from the RNase P RNA gene offers a rapid and fairly inexpensive alternative to current methods (7, 8, 10, 18, 19, 23, 27, 29).

Sequence variances in the RNase P RNA gene between species can also yield clues to the molecular structure of the RNA. In the case of the mycobacteria (FIG. 2), almost all variances in the sequences were in unpaired regions, or in structures which seem unimportant for catalytic activity in vitro.

For instance, in two species, *M. smegmatis* and *M. fortuitum*, the bases 160-164 corresponding to the end of the P12 loop, (FIG. 2) are not present in the RNase P RNA gene sequence. The P12 loop is missing in the gene from some other organisms, such as *Mycoplasma fermentans* (4, 25) and thus does not seem necessary for ribozyme activity.

The alignment also supports conclusions about RNase P structure drawn from other experiments. Suggested important regions such as the motif bp 75-85 and pairing nt 409-417 (FIG. 2) are preserved throughout all analysed mycobacterial species. In all probability, these two regions base pair, since matching sequences are well conserved between organisms. The most variable regions between mycobacterial species were the P3 and P19 loops respectively. The P19 structure is not necessary for RNase P activity in vitro (25) and there is considerable variability in the P3 loop between organisms, but their role in vivo is unclear.

The suggested structure of *M. tuberculosis* RNase P RNA could still be improved upon with the help of sequence variations between species. A structure which is believed to be of importance is the P18 stem-loop, (the region nt 330-351) which has a well-preserved stem in the *Escherichia coli* and *Clamydia* RNase P RNAs. The suggested mycobacterial structure has a far less convincing stem structure. (See FIG. 2, which is based on the old structure prediction.) However, in *M. smegmatis* and *M. marinum* there are variations from the consensus sequence. (FIG. 1) A slightly different stem-loop structure would accommodate for these exchanges while keeping a consensus secondary structure intact, at the same time allowing for a more convincing base-paring pattern (FIG. 5). This also strengthens the argument for the importance of this stem-loop for RNase P function.

Example 2

*Chlamydia*

Material and Methods

Bacterial Strains

DNA of analysed organisms were released by standard Proteinase K treatment of cell culture grown organisms and phenol extracted or were provided as purified DNA-preparations (Table 2).

TABLE 2

Strains, host of origin, references, sources and accession numbers
Superscript ‘T’ indicates the type species

| Strain | Host of origin | Reference | Source* | Accession no |
|---|---|---|---|---|
| *Chlamydophila psittaci* | | | | |
| 6BC$^T$ (VR-125$^T$)† | Psittacine | Golub & Wagner (1947) | Storey | AJ012169 |
| GD | Duck | Illner (1960) | NADC | |
| NJI | Turkey | Page (1959) | NADC | |
| WC | Cattle | Page (1967) | NADC | |
| VS225 | Psittacine | | NADC | |
| 360 | Duck | | Storey | |
| N352 | Duck | Richmond et al. (1982) | Storey | |
| Ca110 | Human | Francis & Magill (1938) | Storey | |
| CP3 (VR-574) | Pigeon | Page & Bankowski (1960) | NADC | |
| M56 (VR-630) | Muskrat | Spalatin et al. (1966) | NADC | |
| *Chlamydophila abortus* | | | | |
| B577$^T$ (VR-656$^T$) | Ovine, abortion | Perez-Martinez & Storz (1985) | Denamur | AJ131092 |
| EBA | Bovine, abortion | Perez-Martinez & Storz (1985) | NADC | |
| OSP | Ovine | Andersen & Van Deusen (1988) | NADC | |
| EAE/Lx | Ovine, abortion | | Storey | |
| AB7 | Ovine, abortion | Rodolakis et al. (1989) | Rodolakis | |
| OCl | Ovine, conjunctivitis | Rodolakis et al. (1989) | Rodolakis | |
| AVl | Bovine, abortion | Rodolakis et al. (1989) | Rodolakis | |
| ACl | Caprine, abortion | Rodolakis et al. (1989) | Rodolakis | |
| iCl | Ovine | Rodolakis et al. (1989) | Rodolakis | |
| *Chlamydophila fetis* | | | | |
| FP Baker$^T$ | Feline | Baker (1942) | NADC | AJ012171 |
| Cello | Feline | Cello (1967) | Storey | |
| Pring | Feline | Wills et al. (1984) | Storey | |

TABLE 2-continued

Strains, host of origin, references, sources and accession numbers
Superscript 'T' indicates the type species

| Strain | Host of origin | Reference | Source* | Accession no |
|---|---|---|---|---|
| *Chlamydophila caviae* | | | | |
| $GPIC^T$ ($VR-813^T$) | Guinea pig | Murray (1964) | Storey | AJ012172 |
| *Chlamydophila pecorum* | | | | |
| $E58^T$ ($VR-628^T$) | Bovine | McNutt & Waller (1940) | NADC | AJ012173 |
| iB1 | Ovine | Rodolakis et al. (1989) | Rodolakis | AJ131091 |
| iC4 | Ovine | Rodolakis et al. (1989) | Rodolakis | |
| ABI0 | Ovine, abortion | Rodolakis et al. (1989) | Rodolakis | |
| IPA (VR-629) | Ovine | Page & Cutlip (1968) | NADC | AJ131090 |
| H3 | Koala | | Storey | AJ131089 |
| *Chlamydophila pneumoniae*‡ | | | | |
| $TW183^T$ ($VR-2282^T$) | Human | Grayston et al. (1989) | ATCC | AJ012174 |
| CM1 (VR-1360) | Human | Black et al. (1992) | Black | |
| CWL011 | Human | Black et al. (1992) | Black | |
| CWL029 (VR-1310) | Human | Black et al. (1992) | Black | |
| CWL050 | Human | Black et al. (1992) | Black | |
| FML16 | Human | Black et al. (1992) | Berdal | |
| P1 | Human | Herrmann et al. (1996) | UHU | |
| JG915 | Human | Herrmann et al. (1996) | UHU | |
| JG954 | Human | Herrmann et al. (1996) | UHU | |
| TWAR 2023 (VR-1356) | Human | Chirgwin et al. (1989) | ATCC | |
| *Chlamydia trachomatis* | | | | |
| A/Har-$13^T$ ($VR-571B^T$)§ | Human | Wang & Grayston (1962) | Persson | AJ131088 |
| L1/440/LN (VR-901B)§ | Human | Schachter & Meyer (1969) | Persson | AJ012175 |
| *Chlamydia suis* | | | | |
| $545^T$ ($VR-1474^T$) | Swine | Kaltenboeck et al. (1993) | NADC | AJ012176 |
| R22 | Swine | Rogers et al. (1993) | NADC | |
| *Clamydia muridarum* | | | | |
| $MoPn^T$ ($VR-123^T$) | Mouse | Nigg (1942) | NADC | AJ012177 |
| SFPD | Hamster | Stills et al. (1991) | NADC | |
| *Simkania negevensis* | | | | |
| $Z^T$ ($VR-1471^T$) | Cell culture | Kahane et al. (1995) | Kahane | AJ012178 |
| *Parachlamydia acanthamoebae* | | | | |
| $Bn_g^T$ | Amoeba/human | Amann et al. (1997) | Michel | AJ012179 |
| $Berg_{17}$ | Amoeba/human | Amann et al. (1997) | Michel | |

PCR Amplification and DNA Sequence Determination

The rnpB gene in species of *Chlamydiaceae* was amplified by PCR with the primer pair BH1-BH2, which was designed based on the *C. trachomatis* sequence (13) (Table 3).

TABLE 3

Primers used for amplification of the rnpB gene

| Primer | Sequence | Nucleotide positions in rnpB of *Chlamydia trachomatis* (see FIG. 6): |
|---|---|---|
| BH1 | 5'-CGGACTTTATAAGAAAAGAT-3' (upper) | 64 to 83 |
| BH2 | 5'-(A/G)TAAGCCGGGTTCTGT-3' (lower) | 392 to 377 |
| BM1 | 5'-(A/G)(A/G)(C/A)G(A/G)(A/G)GAGGAAAGTCC-3' (upper) | 48 to 64 |
| JB1 | 5'-CGAACTAATCGGAAGAGTAAGGC-3' (upper) | -8 to 15 |
| JB2 | 5'-GAGCGAGTAAGCCGG(A/G)TTCTGT-3' (lower) | 398 to 377 |

The reaction mixture contained 0.2 μM of each primer, 200 μM dNTP, 1.5 mM $MgCl_2$, 10 mM Tris-HCl (pH 8.3), 50 mM KCl, 15% glycerol and 2 U Taq polymerase. Amplification conditions consisted of 7 cycles with 45 s at 94° C., 45 s at 42° C., 1 min at 72° C. followed by 35 cycles where the annealing temperature was increased to 58° C. If not otherwise stated, all PCR-products mentioned in the text refer to the use of the primer pair BH1-BH2, which amplified 82% of the full-length gene. To generate the 5'-flanking region from type strains of the nine *Chlamydiaceae* species we used the primer pair JB1-JB2 which was obtained from the complete RNase P RNA gene sequence of *C. trachomatis* (kindly provided by Dr J. Brown). Amplification conditions were as described for the BH1-BH2 primer pair, except that glycerol was omitted and the annealing temperatures were 53° C. and 58° C., respectively. For amplification of *S. negevensis* and *P. acanthamoebae* the BH1 primer was replaced by BM1, which included highly conserved nucleotides as previously described (13), but did not permit sequencing of the 5' end of rnpB. The resulting PCR products were sequenced by using a terminator labelled cycle sequencing chemistry and sequence reactions were analyzed on a 310 Genetic Analyzer (Perkin-Elmer). Sequences were submitted to EMBL and all accession numbers listed in Table 2 are from the present study.

Sequence Alignment and Phylogenetic Analysis

Sequence alignment required secondary structure modelling of each RNase P RNA molecule which was performed manually by using comparative sequence analysis. The predicted structures were subsequently used in the alignment procedure as an aid for the identification of loop and stem regions. The alignment was used to study molecular phylogeny. The calculated distance matrix was corrected for multiple base changes at single locations by the one parameter model of Jukes & Cantor (1969)(55). This matrix was subsequently used to compute a phylogenetic tree by using the neighbor-joining program (77), implemented under the name NEIGHBOR in the Phylogenetic Inference Package, PHYLIP version 3.51c (44). Maximum parsimony trees were inferred using the DNAPARS program. The SEQBOOT program was used to bootstrap the trees based on neighbor-joining and maximum parsimony by resampling the data sets 1000 times. The construction of the maximum likelihood tree was performed with the DNAML program using the F84 model of molecular evolution applying empirical base frequencies, global rearrangement and the jumble option.

Preparation of RNase P RNA and Substrates

To test rnpB catalytic activity, the full-length *C. trachomatis* rnpB was PCR amplified, cloned behind a T7 promoter, and assayed for tRNA precursor cleavage. We designed a PCR primer matching the 5' end (5' TTTGAATTCGAAATTAATACGACTCACTATAG CGAACTAATCGGAAGAGTA). Underlined residues match the *C. trachomatis* rnpb while the remaining part of the primer corresponds to the T7 promoter. We designed a primer complementing the 3' end (5'TTAAGCTTGGATGGTACCTTGGAAAAGCTCGGAAGAGCGAGTAA). Underlined residues are complementary to the *C. trachomatis* rnpB and the unmarked residues were incorporated in order to be able to cleave the resulting plasmid with FokI). The PCR amplified *C. trachomatis* rnpB was cut with EcoRI and HindIII and inserted into pUC19 which had been cut with the same enzymes. The recombinant plasmid was transformed in *Escherichia coli* strain DH5a following standard protocols.

The *E. coli* RNase P RNA, the *C. trachomatis* RNase P RNA and the precursor $tRNA^{Tyr}$Su3 were generated using the T7 DNA dependent RNA polymerase as described elsewhere (59 and references therein).

RNase P RNA assay. The RNase P RNA activity was monitored at 37° C. in our standard reaction buffer (50 mM Tris-HCl (pH 7.5), 5% (w/v) PEG 6000, 100 mM $NH_4Cl$ (or 1M $NH_4Cl$ as indicated) and 100 mM $MgCl_2$) as previously described (59 and references therein) and the final concentration of *C. trachomatis* RNase P RNA was ≈2.4 pmol·$mL^{-1}$ and of precursor $tRNA^{Tyr}$Su3≈0.052 pmol·$mL^{-1}$.

Nucleotide Sequence Accession Numbers

Representative nucleotide sequences for examined species have been submitted to EMBL. Accession numbers are listed in Table 2.

Results

Figure 6:
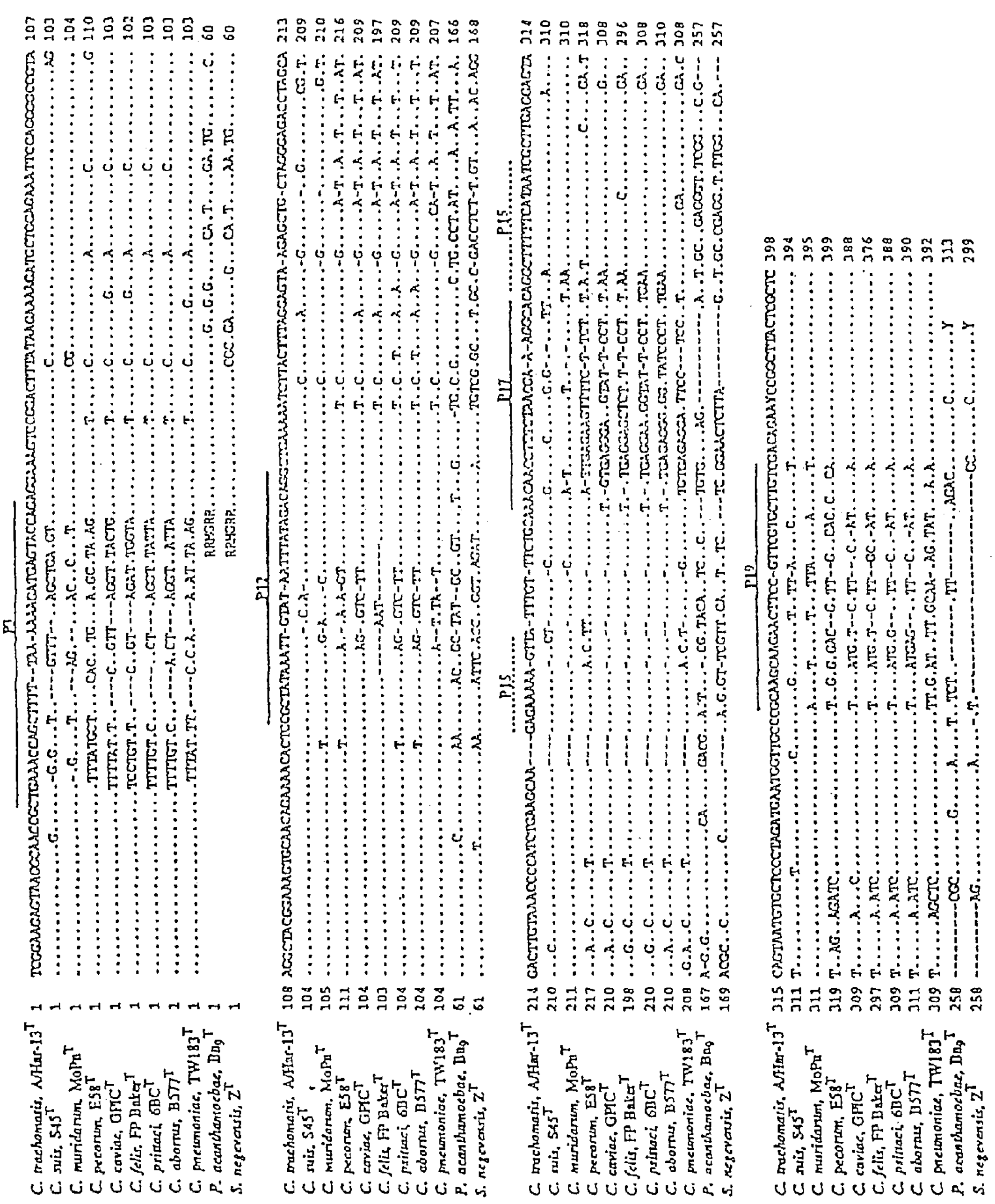
FIG. 6 depicts the DNA sequence comparison of rnpB from the 9 *Chlamydiaceae* species, *P. acanthamoebae* and *S. negevensis*.

The results from Example 2 will be discussed below in association with the accompanying drawings FIGS. 6-8:

FIG. 6: DNA sequence comparison of mpB from the 9 *Chlamydiaceae* species, *P. acanthamoebae* and *S. negevensis*. Dots indicate identity with the *C. trachomatis* A/Har-$13^T$ sequence and dashes indicate gaps in the alignment. The hypervaribale regions P3, P12, P17 and P19 are indicated. Numbering is according to Brown (39).

Figure 7:
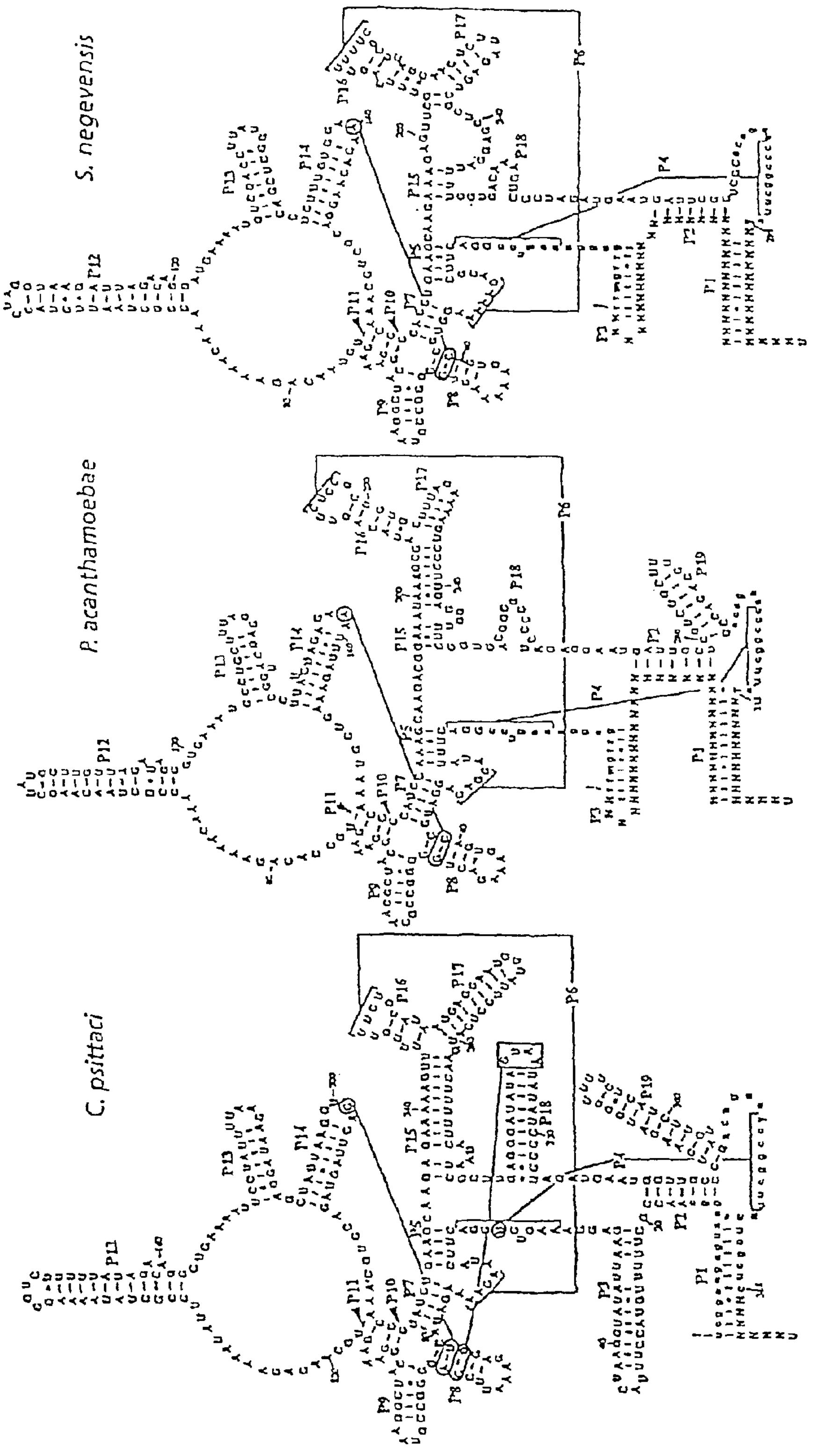
FIG. 7 depicts the deduced secondary structures of RNase P RNA in *C. psittaci, P. acanthamoebae* and *S. negevensis*.

FIG. 7: Deduced secondary structures of RNase P RNA in *C. psittaci, P. acanthamoebae* and *S. negevensis*. The nucleotides in the primer sequences are in lower case type, m indicates an adenine-cytosine mixture, and r indicates adenine-guanine mixture at this position. N denotes tentative nucleotides in the flanking, regions of the primer based on the minimum consensus bacterial RNase P RNA (39).

Figure 8:
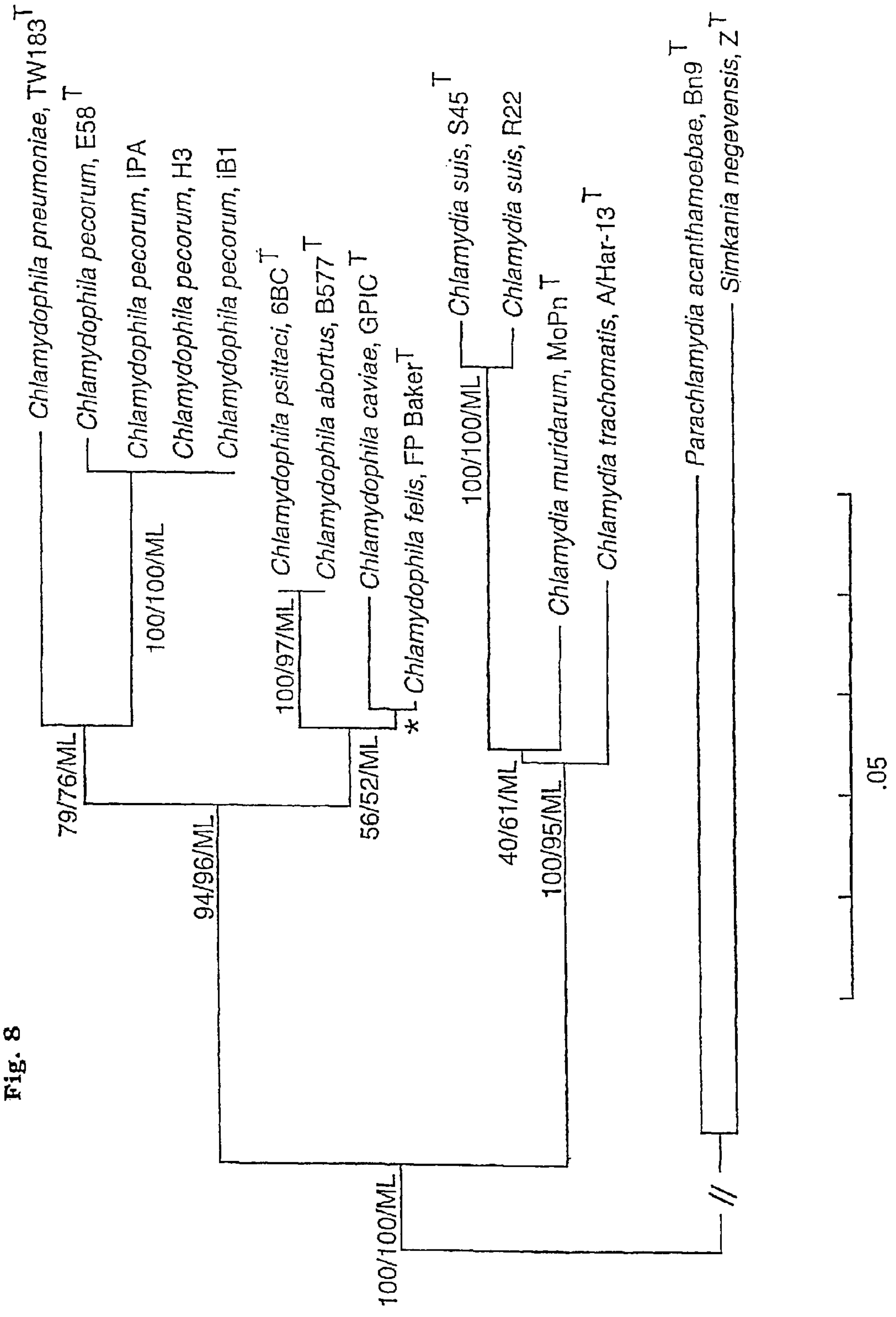
FIG. 8 depicts the neighbour-joining tree based on rnpB, showing the relationships among members of the family *Chlamydiaceae. P. acanthamoebae*, strain $Bn_9^T$ and *S. negevensis*, strain $Z^T$ were chosen as outgroups.

FIG. 8: Neighbour-joining tree based on rnpB, showing the relationships among members of the family Chlamydiaceae. *P. acanthamoebae*, strain $Bn_9{}^T$ and *S. negevensis*, strain $Z^T$ were chosen as outgroups. Parsimony and ML analyses produced an identical branch order. However, two taxa branched slightly different in the ML tree and this node is marked with an asterick. Bootstrap support values at the nodes were obtained from 1000 resamplings of the data set using neighbor-joining and maximum parsimony. The scale bar indicates 5 substitutions per 100 nucleotides.

Comparison of rnpB Sequences

PCR products that included 82% of the full-length rnpB gene were obtained from 60 chlamydial strains. The products from *P. acanthamoebae* strain $Bn_9{}^T$ and $Berg_{17}$ were 313 bases long and their sequences were identical. The sequence of the 299-bp product from the $Z^T$ strain of *S. negevensis* was 68.9% similar to the *P. acanthamoebae* sequence. The Chlamydiaceae PCR products were between 63.8% and 69.3% similar to the segments available from *P. acanthamoebae* and *S. negevensis*. The rnpB sequences from *Chlamydia* and *Chlamydophila*, which are the 2 genera in the Chlamydiaceae, were 75.9%-83.3% similar. The 18 strains belonging to *Chlamydia* were >89.9% similar; the 38 strains belonging to *Chlamydophila* were >84.8% similar. The 14 *C. trachomatis* sequences differed by only a single base substitution in the LGV biovar compared to the Trachoma biovar. The 2 *Chlamydia suis* strains differed in only two nucleotide positions. The 6 *Chlamydia pecorun* strains were identical or differed by only 1 or 2 bases. Sequences were identical within species for 10 *Chlamydia psittaci* strains (except strain M56, see below), 10 *Chlamydia pneumoniae* TWAR biovar sequences, 9 *Chlamydia abortus* sequences, 3 *Chlamydia felis* sequences and the 2 *Chlamydia muridarum* sequences.

Nearly full-length gene segments (98% of the rnpb gene) were generated by PCR using primers JB1 and JB2 from a subset of 14 strains that included all of the 9 *Chlamydiaceae* species. Comparison of these sequences reduced the interspecies similarity as much as 2.6% as because they included the variable P3 region. The diversity in rnpB was large enough to clearly distinguish species groupings in the

*Chlamydiaceae*. Unlike ompA gene products, which differ by up to 50%, and ribosomal RNA genes, which differ by <10%, this diversity will readily permit the design of genus- and group-specific PCR probes.

The strains MoPn$^T$ (mouse) and SFPD (hamster) of the species *C. muridarum* have been shown to differ in their MOMP gene sequences (85). In contrast, the rnpB genes in the two *C. muridarum* strains were identical, as also has been found in the ribosomal 16S/23S intergenic spacers and 23S domain I segments (42). Evolutionary pressure on the surface exposed protein has clearly been greater than on the genes involved in the translation process.

Twenty two strains which were classified as *C. psittaci* until recently have now been separated into *C. psittaci, C. abortus, C. felis* and *C. caviae*. Our study separated these strains into the 4 species groupings by rnpB gene sequence differences of up to 6.7% (data not shown). These species have been isolated from host groups of distant origin and they cause a wide spectrum of diseases (Table 2). Only *C. psittaci* strain M56 conflicted with its classification as *C. psittaci* and PCR of this strain produced an rnpB sequence that matched the feline sequences analyzed in this study. M56 history provides some insight why this may have occurred. M56 was isolated in 1961 from a muskrat in Canada (79), then stocked and distributed to ATCC from the USDA National Animal Disease Center in Ames, Iowa, U.S.A. In cell culture, the ATCC preparation of M56 grew out as M56 serotype in one cell line and as the feline serotype in another (Andersen, unpublished). Fukushi & Hirai (1989)(46) reported a feline serotype for M56 obtained from ATCC. PCR of M56 cultured at NADC on Aug. 1, 1990 in the yolk sacs of embryonating eggs gave *C. psittaci*-avian-like ribosomal and full-length major outer membrane protein gene sequences (42). M56 DNA used in the current study was an aliquot from the 1997 study (Table 2). In view of this history, our rnpb analysis suggests that M56 cultures were contaminated with feline chlamydiae during the 1960's and that uncontaminated isolates may no longer be available.

Secondary Structures of the RNase P RNA

Alignment of the sequences of the rnpB gene derived from the nine *Chlamydiaceae* species indicated four hypervariable regions located in distinct stem loops, denoted as P3, P12, P17 and P19 in the suggested secondary structures (FIG. 7).

The P15 loop (see FIG. 7) is of interest since in most bacterial RNase P RNA molecules it harbours a GGU-motif that interacts with tRNA precursors by base pairing with the 3'-terminal RCCA motif of the tRNA (60). The absence of this sequence motif from all members of the Chlamydiales is striking and an ATAA-bulge is seen in all nine *Chlamydiaceae* species (positions 291 to 294 in *C. psittaci*, FIG. 7), except in *C. pneumoniae* (GAAA) and in *C. felis* (ACAA). Furthermore, a different structure in the P15 region of *Chlamydiaceae* species is rationalized by the finding that none of the identified tRNA genes encode the 3' terminal CCA sequence (80).

Interestingly, the P15 region in *P. acanthamoebae* harbours a purine rich bulge carrying a GGU-motif. This might indicate that these RNase P RNAs interact with the 3' terminal RCCA sequence as does *E. coli* RNase P RNA, given that the CCA sequence is encoded in the tRNA genes in this species. By contrast, the P15 loop structure of RNase P RNA derived from *S. negevensis* is similar to that observed in most cyanobacteria (87) and it carries a GGAU-motif in the P15 loop as does RNase P RNA derived from *Thermus thermophilus* (53). It has been suggested that this loop of RNase P RNA in *T. thermophilus* carries a high-affinity binding site for the 3' end of a tRNA precursor (52) and it may therefore also be valid for *S. negevensis.*

The RNase P RNA in *Chlamydiaceae* species harbour a P18 helix while *P. acanthamoebae* and *S. negevensis* appears to lack this element. It has previously been shown that the P18 helix can be deleted without losing catalytic activity, suggesting that it is not directly involved in catalysis (49). The P18 helix, when present, is associated with a phylogenetically conserved GNRA tetra loop which docks into its suggested receptor in P8 (the G83C93 base pair in *C. psittaci*; FIG. 2; (38, 62). Furthermore, bacterial RNase P RNAs that lack the P18 helix have an extended P8 helix and it has been suggested that this compensates for the loss of P18 (38). Since neither *P. acanthamoebae* nor *S. negevensis* have an extended P8 or an apparent P18 with a GNRA tetra loop, perhaps the nucleotides in the P18 region form an alternative structural element that interacts with P8.

A long range interaction has also been suggested between the GNRA tetra loop in the P14 helix and the P8 stem (38, 62). This is supported by our present data in all nine species of *Chlamydiaceae* (the U82A94 base pair and G201 in *C. psittaci*, FIG. 7) and by the presence of an A in the P14 loop and the GC base pair in P8 in *P. acanthamoebae* and *S. negevensis* (FIG. 2). Given the presence of this interaction, it is surprising that in the three serovars L1 to L3 of *C. trachomatis* the G205 nucleotide (corresponding to G201 in *C. psittaci* in FIG. 7) is substituted by an A, but without a corresponding base pair shift in the P8 helix.

In the minimum consensus bacterial RNase P RNA certain positions have 100% conserved nucleotide bases (39). Our data showed that the well-conserved cytosine at position 60 has been replaced by a uracil in all examined species of the *Chlamydophila* genus (FIG. 7), while no change was observed for the *Chlamydia* genus. This generates either a UG wobble base pair or a UA base pair, depending on the residue at position 376 (numbering refers to *C. psittaci*). The region of the RNase P RNA derived from these species could not be examined with the primers used in the present study.

Cleavage of tRNA Precursors by *C. trachomatis* RNAse P RNA

Bacterial RNase P RNA is catalytically active in the absence of the RNase P protein moiety (33 and references therein). To investigate whether *Chlamydia* RNase P RNA alone is able to cleave its substrate we generated *C. trachomatis* RNase P RNA and analysed the cleavage pattern using the *E. coli* tRNA$^{Tyr}$Su3 (pSu3) precursor as substrate. This RNase P RNA was indeed able to cleave pSu3 at the expected position only when using $NH_4Cl$ at high concentration, as described in Methods. This is in keeping with a previous observation of cleavage by *C. trachomatis* RNase P RNA (51). Taken together with the structural observations this demonstrates that RNase P RNA does not require a P15 internal loop (or a P15 hairpin loop) for catalytic activity. However, we note that the extent of cleavage by *C. trachomatis* RNase P RNA was significantly reduced compared to cleavage by *E. coli* RNase P RNA.

Phylogeny of the Family Chlamydiaceae

The secondary structures of the helices P15, P16, P17, P18, and P19 were the most difficult regions to resolve for the members of the Chlamydiaceae. Consequently, two of these regions, namely P17 and P19, were removed from the final data set that was used for phylogenetic calculations. This was due to the high nucleotide variability in the locale of P17 and the apparent absence of the helix P19 in the rnpB gene of *P. acanthamoebae* (FIGS. 6 & 7). Also, the ambiguously aligned positions 94, 150, 151, 153, 286, and 298 (according to the numbering of the rnpB gene of *C. trachomatis* in FIG. 6) were removed prior to phylogenetic analysis. Gapped positions were generally not omitted from the final alignment except for the termini of the 5'-end, since the positions 1 to 68 were not determined for *S. negevensis* and *P. acanthamoebae*. Consequently, the corrected final alignment comprised 271 positions.

Different algorithms were used to calculate evolutionary trees to reveal the phylogenetic relationships among the species of the family Chlamydiaceae. Virtually identical tree topologies were obtained by using distance matrix and character based methods. A representative phylogenetic tree derived by using neighbor-joining (NJ) (Saitou & Nei, 1987) is shown in FIG. 3. The stability of the branching order was evaluated statistically by the determination of bootstrap percentage values. These values as obtained by NJ and maximum parsimony are given at the nodes. The branching order supported by the maximum likelihood tree (ML) has also been added to each branching point in FIG. 3. Two taxa branched somewhat differently in the dendrogram constructed by ML and the actual node displaying this instability has been furnished with an asterisk. Identical tree topologies to those shown in FIG. 3 were also obtained when only using rnpB data from the species belonging to *Chlamydophila* and *Chlamydia* but extending the data set to comprise the nucleotide information of the 5'-end. Therefore, the branching order in this part of the tree was not resolved.

The tree in FIG. 8 shows that the genera *Chlamydophila* and *Chlamydia* can readily be distinguished from one another by comparing rnpB gene sequences. These findings are consistent with recently published phylogenies based on full-length 16S and 23S ribosomal RNA genes, and on their intergenic spacer regions (42, 43, 73). However, this conflicts with the results presented for the 16S rRNA gene by Pettersson et al. (1997). A plausible explanation is that the 16S rRNA study was based on only ⅘ of the full-length nucleotide information for these genes and that some of the sequences used for comparison were rather distantly related. Therefore, some phylogenetic information was lost in the final data set. In a subsequent 16S rRNA analysis using almost complete 16S rRNA gene sequences and only close relatives as outgroups, there was limited correlation with other branching orders. Thus it can be concluded that 16S rRNA genes provide low resolution in describing the evolutionary interrelationships of the members of the Chlamydiaceae family.

Analysis of the rnpB gene demonstrated that chlamydial phylogeny need not rely entirely on genes for which there is only weak branch support. While 16S rRNA analyses show numerous long branches with clusters attached, the rnpB analysis has evenly distributed sequence differences that distinguish chlamydial groups at family, genus, and species levels. The sequence diversity of the rnpB gene in the species of the order Chlamydiales will make it possible to use this gene for the discrimination of chlamydial species. Moreover, this specificity reveals a functional isolation of each grouping that is consistent with the species-specific ecological niches as described (70). The conservation is also consistent with previously identified groupings. The specificity found in so basic a function as tRNA processing, suggests that the species groupings in the Chlamydiaceae have been evolutionarily isolated for a very long period of time. The presented phylogenetic analysis supports the revision of the classification of the Chlamydiaceae family as previously described (43).

In summary, the sequence of the RNase P RNA gene (mpB) was determined for 60 strains representing all nine species in the Chlamydiaceae family and for the related *Chlamydiales* species, *Parachlamydia acanthamoebae* and *Simkania negevensis*. These sequences were used to infer evolutionary relationships among the Chlamydiaceae. The analysis separated *Chlamydophila* and *Chlamydia* into two lineages, with *Chlamydophila* forming three distinct clusters: the *Chlamydophila pneumoniae* strains, the *Chlamydophila pecorum* strains and a third cluster comprising the species *Chlamydophila psittaci, Chlamydophila abortus, Chlamydophila caviae* and *Chlamydophila felis*. The *Chlamydia* line of descent contained two clusters, with the *Chlamydia suis* strains distinctly separated from strains of *Chlamydia trachomatis* and *Chlamydia muridarum*. This analysis indicated that the rnpB sequence and structure are distinctive markers for species in the *Chlamydiaceae*. We also demonstrated that the RNase P RNA derived from *C. trachomatis* is able to cleave a tRNA precursor in the absence of protein. Our findings are discussed in relation to the structure of *Chlamydia* RNase P RNA.

REFERENCES

1. Abed, Y., C. Bollet, and P. De Micco 1995. Demonstration of *Mycobacterium kansasii* species heterogeneity by the amplification of the 16S-23S spacer region. J. M. Microbiol. 43: 156-158
2. Alcaide F., I. Richter, C. Bernasconi, B. Springer, C. Hagenau R. Schulze-Robbecke, E. Tortoli, R. Martin, E. C. Böttger, and A. Telenti. 1997. Heterogeneity and clonality among isolates of *Mycobacteria kansasii*: Implications for epidemiological and pathogenicity studies. J. Clin. Microbiol. 35:1959-1964
3. Bascunana C. R. and K. Belak K. 1996. Detection and identification of mycobacteria in formalin-fixed, paraffin-embedded tissues by nested PCR and restriction enzyme analysis. J. Clin. Microbiol. 10:2351-2355.
4. Brännvall, M., J. G. Mattsson, S. G. Svärd S. G., and L. A. Kirsebom. 1998. RNase P RNA structure and cleavage reflect the primary structure of tRNA genes. J. Mol. Biol. 283:771-83
5. Brown J. W. and N. R. Pace. 1992. Ribonuclease P RNA and protein subunits from bacteria. Nucleic Acids Res. 20:1451-1456.
6. Cole S. T., R. Brosch, J. Parkhill, T. Garnier, C. Churcher, D. Harris, S. V. Gordon, K. Eiglmeier, S. Gas, C. E. 3rd Barry, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby; K. Jagels, B. G. Barrell, et al., 1998. Deciphering the biology of *Mycobacterium tuberculosis* from the complete genome sequence. Nature 393:537-44.
7. Crawford J. T. 1994. Development of rapid techniques for identification of *M. avium* infections. Res. Microbiol. 145: 177-181.
8. Devallois A., M. Picardeau, K. S. Goh, C. Sola, V. Vincent, and N. Rastogi. 1996. Comparative evaluation of PCR and commercial DNA probes for detection and identification to species level of *Mycobacterium avium* and *Mycobacterium intracellulare*. J. Clin. Microbiol. 34:2756-2759.
9. Devallois A., M. Picardeau, C. N. Paramasivan, V. Vincent, and N. Rastogi. 1997 Molecular characterization of *Mycobacterium avium* complex isolates giving discordant results in AccuProbe tests by PCR-restriction enzyme analysis, 16S rRNA gene sequencing, and DT1-DT6 PCR. J. Clin. Microbiol. 35:2767-2772.

10. Frothingham R., and K. H. Wilson. 1994. Molecular phylogeny of the *Mycobacterium avium* complex demonstrates clinically meaningful divisions. J. Infect. Dis. 169: 305-312.
11. Gardiner K. and N. R Pace. 1980. RNase P of *Bacillus subtilis* has an RNA component. J. Biol. Chem. 255:7507-7509
12. Guerrier-Takada, C., K. Gardiner, T. L. Marsh, N. R. Pace, and S. Altman. 1983. The RNA moiety of RNase P is the catalytic subunit of the enzyme. Cell 35:849-857
13. Herrmann B., O. Winqvist, J. G. Mattsson, and L. A. Kirsebom L A. 1996. Differentiation of *Chlamydia* spp. by sequence determination and restriction endonuclease cleavage of RNase P RNA genes. J. Clin. Microbiol. 34:1897-1902.
14. Iinuma Y., S. Ichiyama, Y. Hasegawa, K. Shimokata, S. Kawahara, and T. Matsushima. 1997. Large-restriction-fragment analysis of *Mycobacterium kansasii* genomic DNA and its application in molecular typing. J. Clin. Microbiol. 35: 596-599
15. Ji-e Y., K. E. Kempsell, M. J. Colston and R. A. Cox. 1994 Nucleotide sequences of the spacer-1, spacer-2 and trailer regions of the rrn operons and secondary structures of precursor 23S rRNAs and precursor 5S rRNAs of slow-growing mycobacteria Microbiology 140:1763-1773.
16. Kapur V., L.-L. Li, M. R. Hamrick, B. B. Plikaytis, T. M. Shinnick, A. Telenti, Jr W. R. Jacobs, A. Banerjee, S. Cole, K. Y. Yuen, J. E. Clarridge III, B. N. Kreiswirth, and J. M. Musser. 1995. Rapid *Mycobacterium* species assignment and unambiguous identification of mutations associated with antimicrobial resistance in *Mycobacterium tuberculosis* by automated DNA sequencing. Arch. Pathol. Lab. Med. 119:131-138.
17. Hole R. M. F. Baer, B. C. Stalk, and S. Altman. 1980. *E. coli* RNAase P has a required RNA component in vivo. Cell 19:881-887
18. Kulski J. K., C. Khinsoe, T. Pryce, and K. Christiansen. 1995. Use of a multiplex PCR to detect and identify *Mycobacterium avium* and *M. intracellulare* in blood culture fluids of AIDS patients. J. Clin. Microbiol. 33:668-674.
19. Nishimori K., M. Eguchi, Y. Nakaoka, Y. Onodera, T. Ito, and K. Tanaka. 1995. Distribution of IS901 in strains of *Mycobacterium avium* complex from swine by using IS901-detecting primers that discriminate between *M. avium* and *Mycobacterium intracellulare*. J. Clin. Microbiol. 8:2102-2106.
20. Picardeau M., G. Prod'hom, L. Raskine, M. P. LePennec, and V. Vincent. 1997. Genotypic characterization of five subspecies of *Mycobacterium kansasii*. J. Clin. Microbiol. 35 25-32.
21. Rastogi N., W. W. Barrow, J. O. Falkinham III, C. O. Thoen, J. T. Crawford, B. T. Mangura, L. B. Reichman, L. B Heifets, B. Dautzenberg, L. S. Young, L. E. Bermudez, C. D. Inderlied, A. E. Suzuki, J. M. Inamine, P. R. J. Gangadharam, M. V. Reddy, M. Denis, H. Shiratsuchi, J., L. Johnson, J. J. Ellner, J. T. Belisle, and P. J. Brennan. 1994. 11th Forum in Microbiology, "Laboratory and clinical aspects of the *Mycobacterium avium* epidemic: contributing factors associated with variability of drug susceptibility and immune responsiveness, and the multifaceted nature of pathogenicity". Res. Microbiol. 145:167-261.
22. Rastogi N., J. J. McFadden, M. L. Gourgeon, L. Montagnier, F. M. Collins, C. R. Horsburgh, R. J. Coker, T. J. Hellyer, I. N. Brown, J. N. Weber, I. M. Orme, D. Chatterjee, J. D. A. Van Embden, D. Van Soolingen, P. M. Small, P. W. M. Hermans, S. E. Hoffner, G. Källenius, S. B. Svenson, R. S. Wallis, J. J. Ellner, H. Shiratsuchi, G. A. W. Rook, A. Vyakarnam, D. M. Yajko, L. S. Young, L. E. M. Bermudez, C. B. Inderlied, Z. M. Kunze, F. Portaels, and V. Labrousse. 1992. 8th Forum in Microbiology, "*Mycobacteria* and AIDS: epidemiological and genetic markers, virulence factors and interactions with the immune system." Res Microbiol. 143:357-440.
23. Richter E., S. Niemann, S. Rusch-Gerdes, and S. Hoffner. 1999 Identification of *Mycobacterium kansasii* by using a DNA probe (AccuProbe) and molecular techniques. J. Clin. Microbiol. 37: 964-970
24. Roth A., M. Fischer, M. E. Hamid, S. Michalke, W. Ludwig, and H. Mauch. 1998 Differentiation of phylogenetically related slowly growing mycobacteria based on 16S-23S rRNA gene internal transcribed spacer sequences. J. Clin. Microbiol. 36:139-147.
25. Siegel, R. W., A. B. Banta, E. S. Haas, J. W. Brown, and N. R. Pace. 1996. *Mycoplasma fermentans* simplifies our view of the catalytic core of ribonuclease P RNA. RNA 2: 452-62.
26. Snapper, S. B., R. E. Melton, S. Mustafa, T. Kieser, and Jacobs W R Jr. 1990. Isolation and characterization of efficient plasmid transformation mutants of *Mycobacterium smegmatis*. Mol. Microbiol 4:1911-1919
27. Sritharan V., J. V. Iralu, and R. H. Barker Jr. 1995. Specificity of diagnostic PCR amplification for *M. avium* using the probe pMAV22. Mol. Cell. Probes 9:71-74.
28. Stark, B. C., R. Kole, E. J. Bowman and S. Altman. 1978. Ribonuclease P: an enzyme with an essential RNA component. Proc. Natl. Acad. Sci. USA 3717-3721
29. Telenti, A. F. Marchesi, M. Balz, F. Bally E. C. Böttger, and T. Bodmer. 1993. Rapid identification of mycobacteria to the species level by polymerase chain reaction and restriction enzyme analysis. J. Clin. Microbiol. 31:175-178.
30. Van der Giessen J. W. B., R. M. Haring, and B. A. M. Van der Zeijst. 1994 Comparison of the 23S ribosomal RNA genes and the spacer region between the 16S and 23S rRNA genes of the closely related *Mycobacterium avium* and *Mycobacterium paratuberculosis* and the fast-growing *Mycobacterium phlei*. Microbiology. 140:1103-1108.
31. Vioque A. 1992. Analysis of the gene encoding the RNA subunit of ribonuclease P from cyanobacteria. Nucleic Acids Res. 20:6331-37
32. Woolford A. J., R. G. Hewinson, M. Woodward, and J. W. Dale 1997. Sequence heterogeneity of an mpb70 gene analogue in *Mycobacterium kansasii*. FEMS Microbiol. Lett. 148:43-48)
33. Altman, S. & Kirsebom, L. A. (1999). Ribonuclease P. In The RNA world: Second edition (Gesteland, R. F., Cech, T. & Atkins, J. F., eds.), pp. 351-380. Cold Spring Harbour Laboratory Press, New York.
34. Amann, R., Springer, N., Schonhuber, W., Ludwig, W., Schmid, E. N., Muller, K. D., Michel R. (1997). Obligate intracellular bacterial parasites of acanthamoebae related to *Chlamydia* spp. *Appl Environ Microbiol* 63, 115-121.
35. Andersen, A. A. & Van Deusen, R. A. (1988). Production and partial characterization of monoclonal antibodies to four *Chlamydia psittaci* isolates. *Infect Immun* 56, 2075-2079.
36. Baker, J. A. (1942). A virus obtained from a pneumonia of cats and its possible relation to the cause of atypical pneumonia in man. *Science* 96, 475-476.
37. Black, C. M., Tharpe, J. A. & Russell, H. (1992). Distinguishing *Chlamydia* species by restriction analysis of the major outer membrane protein gene. *Mol Cell Probes* 6, 395-400.

38. Brown, J. W., Nolan, J. M., Haas, E. S., Rubio, M-A. T., Major, F., Pace, N. (1996). Comparative analysis of ribonuclease P RNA using gene sequences from natural microbial populations reveals tertiary structural elements. *Proc Natl Acad Sci* 93, 301-3006.

39. Brown, J. W. (1998). The Ribonuclease P Database. *Nucl Acids Res* 26, 351-352.

40. Cello, R. M. (1967). Ocular infections with PLT (Bedsonia) group agents. *Am J Ophthalmol* 63, 1270-1273.

41. Chirgwin, K., Roblin, P. M. & Hammerschlag, M. R. (1989). In vitro susceptibilities of *Chlamydia pneumoniae* (*Chlamydia* sp. strain TWAR). *Antimicrob Agents Chemother* 33, 1634-1635.

42. Everett, K. D. & Andersen, A. A. (1997). The ribosomal intergenic spacer and domain I of the 23S rRNA gene are phylogenetic markers for *Chlamydia* spp. *Int J Syst Bacteriol,* 47, 461-473.

43. Everett, K. D. E., Bush R. M. & Andersen, A. A. (1999). Emended description of the order Chlamydiales, proposal of Parachlamydiaeceae fam. nov. and Simkaniaceae fam. nov., each containing one monotypic genus, revised taxonomy of the family Chlamydiaceae including a new genus and five new species, and standards for the identification of organisms. *Int J Syst Bacteriol* 49, 415-440.

44. Felsenstein, J. (1993). PHYLIP (Phylogeny inference package) (version 3.51c). Distributed by the author. University of Washington, Seattle, Department of Genetics.

45. Francis, T., Jr., & Magill, T. P. (1938). An unidentified virus producing acute meningitis and pneumonia in experimental animals. *J Exp Med* 68, 147-160.

46. Fukushi, H. & Hirai, K. (1989). Genetic diversity of avian and mammalian *Chlamydia psittaci* strains and relation to host origin. *J Bacteriol* 171, 2850-2855.

47. Golub, O. J. & Wagner, J. C. (1947). Studies on the interference phenomenon with certain members of the psittacosis-lymphogranuloma group of viruses. *J Immunol,* 59, 59-70.

48. Grayston, J. T., Kuo, C.-C., Campbell, L. A. & Wang, S. P. (1989). *Chlamydia pneumoniae* sp nov for *Chlamydia* sp strain TWAR. *Int J Syst Bacteriol,* 39, 88-90.

49. Haas, E. S., Brown, J. W., Pitulle, C. & Pace, N. R. (1994). Further perspective on the catalytic core and secondary structure of ribonuclease P RNA. *Proc Natl Acad Sci* 91, 2527-2531.

50. Haas, E. S., Banta, A. B., Harris, J. K., Pace, N. R. & Brown, J. W. (1996). Structure and evolution of ribonuclease P RNA in Gram-positive bacteria. *Nucl Acids Res* 24, 4775-4782.

51. Haas, E. S. & Brown, J. W. (1998). Evolutionary variation in bacterial RNase P RNAs. *Nucl Acids Res* 26, 4093-4099.

52. Hardt, W-D., Schlegl, J., Erdmann, V. A. & Hartmann, R. K. (1995). Kinetics and thermodynamics of the RNase P RNA cleavage reaction: Analysis of tRNA 3'-end variants. *J Mol Biol* 247, 161-172.

53. Hartmann, R. K. & Erdmann, V. A. (1991). Analysis of the gene encoding the RNA subunit of ribonuclease P from *T. thermophilus* HB8. *Nucl Acids Res* 19, 5957-5964.

54. Illner, V. F. (1960). Zur Frage der Uebertragung des Ornithosevirus durch das Ei. *Monatsh Veterinaermed* 17, 116-117.

55. Jukes, T. &, Cantor, C. R. (1969). Evolution of protein molecules. In *Mammalian protein metabolism*, pp. 21-132. Edited by H. N. Munro, New York: Academic Press.

56. Kahane, S., Metzer, E. & Friedman, M. G. (1995). Evidence that the novel microorganism ‘Z’ may belong to a new genus in the family Chlamydiaceae. *FEMS Microbiol Lett* 126, 203-207.

57. Kahane, S., Greenberg, D., Friedman, M. G., Haikin, H., & Dagan, R. (1998). High prevalence of “sizmkania Z,” a novel chlamydia-like bacterium, in infants with acute bronchiolitis. *J Infect Dis* 177, 1425-1429.

58. Kaltenboeck, B., Konsoulas, K. G. & Storz, J. (1993). Structures of and allelic diversity and relationships among the major outer membrane protein (ompA) genes of the four chlamydial species. *J Bacteriol,* 175, 487-502.

59. Kirsebom & Svärd (1992). The kinetics and specificity of cleavage by RNase P is mainly dependent on the structure of the amino acid acceptor stem. *Nucl Acids Res* 20, 425-432.

60. Kirsebom, L. A. & Svärd, S. G. (1994). Base pairing between *Escherichia coli* RNase P RNA and its substrate. *EMBO J* 13, 4870-4876.

61. Lieberman, D., Kahane, S., Lieberman, D., & Friedman, M. G. (1997). Pneumonia with serological evidence of acute infection with the chlamydia-like microorganism “Z”. *Am. J. Respir. Crit. Care. Med.* 156, 578-82.).

62. Massire, C., Jaeger, L. & Westhof, E. (1998). Derivation of the three-dimensional architecture of bacterial ribonuclease P RNAs from comparative sequence analysis. *J Mol Biol* 279, 773-793.

63. McNutt, S. F. & Waller, E. F. (1940). Sporadic bovine encephalomyelitis (Buss disease). *Cornell Vet* 30, 437-448.

64. Murray, E. S. (1964). Guinea pig inclusion conjunctivitis virus. I. Isolation and identification as a member of the psittacosis-lymphogranuloma-trachoma group. *J Infect Dis* 114, 1-12.

65. Nigg, C. (1942). Unidentified virus which produces pneumonia and systemic infection in mice. *Science* 95, 49-50.

66. Page, L. A. (1959). Experimental ornithosis in turkeys. *Avian Dis.,* 3, 51-66.

67. Page, L. A. (1967). Comparison of “pathotypes” among Chlamydial (psittacosis) strains recovered from diseased birds and mammals. *Bull Wildl Dis Assoc,* 2, 166-175.

68. Page, L. A. & Bankowski, R. A. (1960). Factors affecting the production and detection of ornithosis antibodies in infected turkeys. *Am J Vet Res.,* 21, 971-978.

69. Page, L. A. & Cutlip, R. C. (1968). *Chlamydial polyarthritis* in Iowa lambs. *Iowa Vet* 39, 10-18.

70. Palys, T., Nakamura, L. K. & Cohan, F. M. (1997). Discovery and classification of ecological diversity in the bacterial world: the role of DNA sequence data. *Int J Syst Bacteriol* 47, 1145-1156.

71. Perez-Martinez, J. A. & Storz, J. (1985). Antigenic diversity of *Chlamydia psittaci* of mammalian origin determined by microimmunofluorescence. *Infect Immun* 50, 905-910.

72. Pettersson, B., Andersson, A., Leitner, T., Olsvik, O., Uhlén M., Storey, C., Black, C. M. (1997). Evolutionary relationships among members of the genus *Chlamydia* based on 16S ribosomal DNA analysis. *J Bacteriol* 179, 4195-4205.

73. Pudjiatmoko, Fukushi, H., Ochiai, Y., Yamaguchi, T. & Hirai, K. (1997). Phylogenetic analysis of the genus *Chlamydia* based on 16GS rRNA gene sequences. *Int J Syst Bacteriol* 47, 425-431.

74. Richmond S. J., Sterling, P., Ashley, C. R. (1982). Virus infecting the reticulate bodies of an avian strain of *Chlamydia psittaci. FEMS Microbiol. Letters,* 14, 31-36.

75. Rogers, D. G., Andersen, A. A., Hogg, A., Nielsen, D. L. & Huebert, M. A. (1993). Conjunctivitis and keratoconjunctivitis associated with chlamydiae in swine. *J Am Vet Med Assoc* 203, 1321-1323.

76. Rodolakis, A., Bernard, F. & Lantier, F. (1989). Mouse models for evaluation of virulence of *Chlamydia psittaci* isolated from ruminants. *Res Vet Sci* 46, 34-39.
77. Saitou, N. & Nei, M. (1987). The neighbor-joining method: a new method for reconstructing phylogenetic trees. *Mol Biol Evol* 4, 406-425.
78. Schachter, J. & Meyer, K. F. (1969). *Lymphogranuloma venereum*. II. Characterization of some recently isolated strains. *J Bacteriol* 99, 636-638.
79. Spalatin, J., Fraser, C. E. O., Connell, R. P. & Berman, D. T. (1966). Agents of psittacosis-lymphogranulomavenereum group isolated from muskrats and snowshoe hares in Saskatchewan. *Can J Comp Med Vet Sci* 30, 225-420.
80. Stephens, R. S., Kalman, S., Fenner, C., Davis, R. (1998) *Chlamydia Genome Project.*
81. Stills, H. F. J., Fox, J. G., Paster, B. J. & Dewhirst, F. E. (1991). A "new" *Chlamydia* sp. strain SFPD isolated from transmissible proliferative ileitis in hamsters. *Microbiol Ecol Health Dis* 4, S99.
82. Vioque, A. (1997). The RNase P RNA from cyanobacteria: short tandemly repeated repetitive (STRR) sequences are present within the RNase P RNA gene in heterocyst-forming cyanobacteria. *Nucl Acids Res* 25, 3471-3477.
83. Wang, S.-P. & Grayston, J. T. (1962). Classification of trachoma virus strains by protection of mice from toxic death. *J Immunol* 90, 849-856.
84. Wills, J. M., Gruffydd-Jones, T. J., Jones T, Richmond, S., Paul, I. D. (1984). Isolation of *Chlamydia psittaci* from cases of conjunctivitis in a colony of cats. *Vet Pec* 114, 344-346.
85. Zhang, Y. X., Fox, J. G., Ho, Y., Zhang, L., Stills, H. J. & Smith, T. F. (1993). Comparison of the major outer-membrane protein (MOMP) gene of mouse pneumonitis (MoPn) and hamster SFPD strains of *Chlamydia trachomatis* with other *Chlamydia* strains. *Mol Biol Evol* 10, 1327-42.

The invention claimed is:

1. A method for differentiating species and/or strains of *Mycobacteria*, comprising:

amplifying nucleic acid corresponding to a hypervariable P3 region of an RNase P RNA gene of the bacteria;

sequencing the P3 region of the amplified nucleic acid; and identifying the species and/or strain of *Mycobacteria* based upon the nucleic acid sequence.

2. The method according to claim 1, wherein the species and/or strains of *Mycobacteria* are selected from the group consisting of: *M. gastri, M. kansasii, M. intracellulare, M. xenopi, M. smegmatis, M. avium, M. marinum, M. fortuitum, M. malmoense, M. paratuberculosis, M. gordoniae* and *M. celatum.*

3. The method according to claim 1, wherein the nucleic acid is amplified utilizing a single primer pair of primers tbf (SEQ ID NO: 1) and tbr (SEQ ID NO: 2).

* * * * *

UNITED STATES PATENT AND TRADEMARK OFFICE

CERTIFICATE OF CORRECTION

PATENT NO. : 8,367,321 B2
APPLICATION NO. : 10/169831
DATED : February 5, 2013
INVENTOR(S) : Herrmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1421 days.

Signed and Sealed this
First Day of September, 2015

Michelle K. Lee
*Director of the United States Patent and Trademark Office*

SEQUENCE LISTING

```
<160> NUMBER OF SEQ ID NOS: 54

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

cggatgagtt ggctgggcgg                                              20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gttggcctgt aagccggatt                                              20


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

cttgcttgcc ctccctttgc c                                            21


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

cggactttat aagaaaagat                                              20
```

-continued

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
rataagccgg gttctgt 17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6
rrmgrrgagg aaagtcc 17

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
cgaactaatc ggaagagtaa ggc 23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
gagcgagtaa gccggrttct gt 22

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
tttgaattcg aaattaatac gactcactat agcgaactaa tcggaagagt a 51

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
tttaagcttg gatggtacct tggaaaagct cggaagagcg agtaa 45

<210> SEQ ID NO 11

-continued

<211> LENGTH: 427
<212> TYPE: DNA
<213> ORGANISM: Mycobacterium tuberculosis

<400> SEQUENCE: 11
cggatgagtt ggctgggcgg ccgcggctcg cgtagggctt gtgtggattc acgaggttca 60
gcgtcgagtc gaggaaagtc cggacttcac agagcagggt gattgctaac ggcaatccga 120
ggtgactcgc gggaaagtgc cacagaaaac agaccgccat cctcgtggtg gcaagggtga 180
aacggtgcgg taagagcgca ccagcattcc gggtgaccgg ggtggctagg caaaccccac 240
ccgaagcaag gccaagaagg ccgcaccgaa agtgcggccg cgcaggcgct tgagggttgc 300
tcgcccgagc ctgcgggtag gccgctcgag gcacccggta acggtgtgtc cagatggatg 360
gtcgccgccg tgccgccgtt agcttggctg tggcggcgcg gaacagaatc cggcttacag 420
gccaact 427

<210> SEQ ID NO 12
<211> LENGTH: 433
<212> TYPE: RNA
<213> ORGANISM: Mycobacterium tuberculosis

<400> SEQUENCE: 12
cggaugaguu ggcugggcgg ccgcggcucg cguagggcuu guguggauuc acgagguuca 60
gcgucgaguc gaggaaaguc cggacuucac agagcagggu gauugcuaac ggcaauccga 120
ggugacucgc gggaaagugc cacagaaaac agaccgccau ccucguggug gcaaggguga 180
aacggugcgg uaagagcgca ccagcauucc gggugaccgg gguggcuagg caaaccccac 240
ccgaagcaag gccaagaagg ccgcaccgaa agugcggccg cgcaggcgcu ugaggguugc 300
ucgcccgagc cugcggguag gccgcucgag gcacccggua acggugugus cagauggaug 360
gucgccgccg ugccgccguu agcuuggcug uggcggcgcg gaacagaauc cggcuuacag 420
gccaacucgu ccg 433

<210> SEQ ID NO 13
<211> LENGTH: 415
<212> TYPE: DNA
<213> ORGANISM: Mycobacterium kansasii

<400> SEQUENCE: 13
cggatgagtt ggctgggcgg ccgcggctcg agttggttcg caaggatcgg cgccgagccg 60
aggaaagtcc ggacttcaca gagcagggtg attgctaacg gcaatccgag gtgactcgcg 120
ggaaagtgcc acagaaaaca aaccgccatc ctcgtggtgg taagggtgaa acggtgcggt 180
aagagcgcac cagcatcccg ggtgaccggg gtggctaggc aaaccccacc cgaagcaagg 240
ccaagaaggc cgcacgaagg tgcggccgcg cagacgccgg agggttgctc gcccgagtct 300
gcgggtaggc cgctcgaggc acccggtgac ggtgtgtcca gatggatggt cgccgccgtg 360
ccgccgttgg ttcagccgcg gcggcaggga acagaatccg gcttacaggc caaca 415

<210> SEQ ID NO 14
<211> LENGTH: 398
<212> TYPE: DNA
<213> ORGANISM: Chlamydia trachomatis

<400> SEQUENCE: 14
tcggaagagt aaggcaaccg ctgaaaccag ctttttaaaa aagatgagta ccagaggaaa 60
gtccggactt tataagaaaa gatgctggag aaattccagg ggccgtaagg ctacggaaag 120

-continued tgcaacagaa aacactccgc tataaattgt ataatttata gacaggctga aaaatcttac 180
tttaggagta agagctgcta gggagaccta gcagacttgt aaaccccatc tgaagcaaga 240
gaaaaagtta tttgtttctg caaacaacct ttctaacgaa aggcacaggc tttttcataa 300
tcgcttgagg agtacagtaa tgtgctccct agatgaatgg ttgcccgcaa gcaagaactt 360
ccgttcgtgc ttgtcgacag aayccggctt actcgctc 398

<210> SEQ ID NO 15
<211> LENGTH: 396
<212> TYPE: RNA
<213> ORGANISM: Chlamydia psittaci
<220> FEATURE:
<221> NAME/KEY: modified_base
<222> LOCATION: (389)..(396)
<223> OTHER INFORMATION: a, c, g, or u

<400> SEQUENCE: 15
ucggaagagu aaggcaaccg cuuuuuguac cuuuacuaag guauauuaag aggaaagucu 60
ggacuucaua agaaaagaua cuggagaaac uccaggggcc guaaggcuac ggaaagugca 120
acagaaaaca uuccgcuaua aaagggucuu uuuauagaca ggcugaaaau uccuauuuua 180
agaauaggag cuauuaaggu gacuuaguag acgugcaaac ccuaucugaa gcaagagaaa 240
aaguuuuugu uucugcauaa ugaggaaugg uauuccucau gaacuuuuuc auaaucgcuu 300
gagggauaua guaauauauc cccuagauga augguugccc ucaagauggg uuuucucauc 360
uuguagacag aayccggcuu acucgcucnn nnnnnn 396

<210> SEQ ID NO 16
<211> LENGTH: 346
<212> TYPE: RNA
<213> ORGANISM: Simkania negevensis
<220> FEATURE:
<221> NAME/KEY: modified_base
<222> LOCATION: (1)..(31)
<223> OTHER INFORMATION: a, c, g, or u
<220> FEATURE:
<221> NAME/KEY: modified_base
<222> LOCATION: (155)
<223> OTHER INFORMATION: a, c, g, or u
<220> FEATURE:
<221> NAME/KEY: modified_base
<222> LOCATION: (332)..(345)
<223> OTHER INFORMATION: a, c, g, or u

<400> SEQUENCE: 16
nnnnnnnnnn nnnnnnnnnn nnnnnnnnnn nrrmgrrgag gaaaguccgg acuucgcaga 60
aaaaggugcc agugaaaaac ugggggccgu aaggcuacgg aaaguguaac agaaaacaaa 120
ccgcuaauuc uaccuaggua agauuagaca ggaungaaaa ugucgagcuu auggcucgac 180
cucuuugugg aaacacaagg acgcugcaaa ccccaccuga agcaagaaag aguucguuuc 240
aguuuuucgc ucaggaacuc uuagagucgc ucgaggauuu uggugacaaa gucccuagau 300
gaaugauugc cucgcacaga acccggcuua ynnnnnnnnn nnnnnu 346

<210> SEQ ID NO 17
<211> LENGTH: 361
<212> TYPE: RNA
<213> ORGANISM: Parachlamydia acanthamoebae
<220> FEATURE:
<221> NAME/KEY: modified_base
<222> LOCATION: (1)..(33)
<223> OTHER INFORMATION: a, c, g, or u
<220> FEATURE:
<221> NAME/KEY: modified_base
<222> LOCATION: (347)..(360)

<223> OTHER INFORMATION: a, c, g, or u

<400> SEQUENCE: 17

```
nnnnnnnnnn nnnnnnnnnn nnnnnnnnnn nnnrrmgrrg aggaaagucc ggacuuuaua     60
ggagaggaug ccagugaaag acugggggcc gcaaggcuac ggaaagugcc acagaaaaca    120
aaccgcuaac aagcuaugcu uguuagauag ggugaaaugc cugcuuuagg agcauggccu    180
uaucuagaga aauuuagaaa gugguaaacc ccauccaaag caagacggaa auaaagcgau    240
acaguucucc gcugugcuuu agaaaagucg cuugaggguu ucggugacgg cgccccuaga    300
ggaaugauug cucgucugcu uugcagaccg acagaacccg gcuuaynnnn nnnnnnnnnn    360
u                                                                    361
```

<210> SEQ ID NO 18
<211> LENGTH: 22
<212> TYPE: RNA
<213> ORGANISM: Mycobacterium tuberculosis

<400> SEQUENCE: 18

```
ggcacccggu aacggugugu cc                                              22
```

<210> SEQ ID NO 19
<211> LENGTH: 22
<212> TYPE: RNA
<213> ORGANISM: Mycobacterium smegmatis

<400> SEQUENCE: 19

```
gguacccggc gacgggcuac cc                                              22
```

<210> SEQ ID NO 20
<211> LENGTH: 22
<212> TYPE: RNA
<213> ORGANISM: Mycobacterium marinum

<400> SEQUENCE: 20

```
gguacccggc aacggugugc cc                                              22
```

<210> SEQ ID NO 21
<211> LENGTH: 385
<212> TYPE: DNA
<213> ORGANISM: Mycobacterium celatum

<400> SEQUENCE: 21

```
cggatgagtt ggctgggcgg ccgcggctcg tttcggcgag tcgaggaaag tccggacttc     60
acagagcagg gtggttgcta acggcaaccc ggggtgaccc gcgggaaagt gccacagaaa    120
acagaccgcc accttcgcgg tggtaagggt gaaacggtgc ggtaagagcg caccagcatt    180
ccgggtgacc ggaatggctc ggcaaacccc acccgaagca aggccaagaa gaccgcacct    240
tcggtgcggt cgcgcaggcg tccgagggtt gctcgcccga gcctgcgggt aggccgcttg    300
aggcacccgg tgacggtgtg tccagatgga tggtcgccgc cgcgcacttg gtggcgcggt    360
acagaatccg gcttacaggc caaca                                          385
```

<210> SEQ ID NO 22
<211> LENGTH: 406
<212> TYPE: DNA
<213> ORGANISM: Mycobacterium xenopi

<400> SEQUENCE: 22

```
cggatgagtt ggctgggcgg ccgcggctct ccctggtccg caggaccagg cgagtcgagg     60
```

-continued

```
aaagtccgga cttcacagag cagggtggtt gctaacagca acccggggtg acccgcggga    120

aagtgccaca gaaaacagac cgccaccttc gcggtggtaa gggtgaaacg gtgcggtaag    180

agcgcaccag catcccgggt gaccgggatg gctaggcaaa ccccacccga agcaaggcca    240

agaagaccgc acccggtgcg gtcgcgcagg cgcttgaggg ttgctcgccc gagcctgcgg    300

gtaggccgct tgaggcaccc ggtgacggtg tgtccagatg gatggtcgcc gccccgctgc    360

cgctattcgc ggtggcgggg aacagaatcc ggcttacagg ccaaca                   406
```

<210> SEQ ID NO 23
<211> LENGTH: 413
<212> TYPE: DNA
<213> ORGANISM: Mycobacterium malmoense

<400> SEQUENCE: 23

```
cggatgagtt ggctgggcgg ccgcggctcg cgccggtcga gaggccggtg ccgagtcgag     60

gaaagtccgg acttcacaga gcagggtgat tgctaacggc aatccgaggt gactcgcggg    120

aaagtgccac agaaaacaaa ccgccacctt cgcggtggta agggtgaaac ggtgcggtaa    180

gagcgcacca gcattccggg tgaccggaat ggctcggcaa accccacccg aagcaaggcc    240

aagaaggccg cacgaaagtg cggccgcgca ggcgctcgag ggttgctcgc ccgagcctgc    300

gggtaggccg cttgaggcac ccggcgacgg tgtgtccaga tggatggtcg ccgccgcgcc    360

gccgttgctt atgccgcggc ggcggggaac agaatccggc ttacaggcca aca           413
```

<210> SEQ ID NO 24
<211> LENGTH: 416
<212> TYPE: DNA
<213> ORGANISM: Mycobacterium leprae

<400> SEQUENCE: 24

```
cggacgagtt ggctgggcgg ccgcggctcg tgtcggtctg aaaggcccgg taacgagtcg     60

aggaaagtcc ggacttcaca gagcagggtg attgctaaca gcaatccgag gtgactcgcg    120

ggatagtgcc acagaaaaca aaccgccatc ctcgcggtgg taagggtgaa acggtgcggt    180

aagagcgcac cagcatcccg ggtgaccggg atggcttggt aaaccccacc cgaagcaagg    240

tcaagaaggc tgcactacaa gtgcggccgc gcaggcgttc gagagctgct cgcccgagcc    300

tgcgggtagg ccgcttgagg cacccggcaa cggtgtgtcc agatggatgg tcgccgccgc    360

gccaccgtag gcaatgccgc gttggcgggg aacagaatcc ggcttatagg ccaact        416
```

<210> SEQ ID NO 25
<211> LENGTH: 392
<212> TYPE: DNA
<213> ORGANISM: Mycobacterium fortuitum

<400> SEQUENCE: 25

```
cggatgagtt ggctgggcgg ccgcggcacc ggtgcaaacc ggggtcgagg aaagtccgga     60

cttcacagag cggggtgatt gctaacggca atccgaggtg actcgcggga aagtgccaca    120

gaaaacagac cgccagaaat ggtaagggtg aaacggtgcg gtaagagcgc accagcaccc    180

cgggtgaccg gggtggctag gcaaacccca cccgaagcaa ggccaagaag accgcaacct    240

ggttgcggtc gcgcaggcgc ctgagggctg ctcgcccgag cctgcgggta ggccgcttga    300

ggcacccggc gacggtgtgt ccagatggat ggtcgccacc ggcccgcccg gtaacgggag    360

ggccggcaca gaatccggct tacaggccaa ca                                  392
```

<210> SEQ ID NO 26

<211> LENGTH: 385
<212> TYPE: DNA
<213> ORGANISM: Mycobacterium smegmatis

<400> SEQUENCE: 26
cggatgagtt ggctgggcgg ccgcggcatc gcctgatgtc gaggaaagtc cggacttcac 60
agagcagggt gattgctaac ggcaatccga ggtgactcgc gggaaagtgc cacagaaaac 120
agaccgccag aaatggtaag ggtgaaacgg tgcggtaaga gcgcaccagc accccgggtg 180
accggggtgg ctaggcaaac cccacccgaa gcaaggccaa gaaggccgca actgcggttg 240
cggccgcgca ggcgcccgag ggttgctcgc ccgagcctgc gggtaggccg cttgaggtac 300
ccggcgacgg gctacccaga tggatggtcg ccgccccacc gccagagatg gcggcgggga 360
acagaatccg gcttacaggc caaca 385

<210> SEQ ID NO 27
<211> LENGTH: 392
<212> TYPE: DNA
<213> ORGANISM: Mycobacterium avium

<400> SEQUENCE: 27
cggatgagtt ggctgggcgg ccgcggctcg tatcccgagt cgaggaaagt ccggacttca 60
cagagcaggg tgattgctaa cggcaatccg aggtgactcg cgggaaagtg ccacagaaaa 120
cagaccgcca ccctcgtggt ggtaagggtg aaacggtgcg gtaagagcgc accagcaccc 180
cgggtgaccg gggtggctcg gcaaacccca cccgaagcaa ggccaagaag gtcgtgccgc 240
cggcacggcc gcgcaggcgt ccgagggttg ctcgcccgag cctgcgggta ggccgctcga 300
ggcacccggt gacggtgtgt ccagatggat ggtcgccgcc gcgccgccgg ttttccggcg 360
gcgcggaaca gaatccggct tacaggccaa ca 392

<210> SEQ ID NO 28
<211> LENGTH: 392
<212> TYPE: DNA
<213> ORGANISM: Mycobacterium paratuberculosis

<400> SEQUENCE: 28
cggatgagtt ggctgggcgg ccgcggctcg tatcccgagt cgaggaaagt ccggacttca 60
cagagcaggg tgattgctaa cggcaatccg aggtgactcg cgggaaagtg ccacagaaaa 120
cagaccgcca ccctcgtggt ggtaagggtg aaacggtgcg gtaagagcgc accagcaccc 180
cgggtgaccg gggtggctcg gcaaacccca cccgaagcaa ggccaagaag gccgtgccgc 240
cggcacggcc gcgcaggcgt ccgagggttg ctcgcccgag cctgcgggta ggccgctcga 300
ggcacccggt gacggtgtgt ccagatggat ggtcgccgcc gcggcgccgg ttttccggcg 360
gcgcggaaca gaatccggct tacaggccaa ca 392

<210> SEQ ID NO 29
<211> LENGTH: 417
<212> TYPE: DNA
<213> ORGANISM: Mycobacterium gordonae

<400> SEQUENCE: 29
cggatgagtt ggctgggcgg ccgcggcccg agtcggtccg agaggtgccg acttgagtcg 60
aggaaagtcc ggacttcaca gagcagggtg attgctaacg gcaatccgag gtgactcgcg 120
ggaaagtgcc acagaaaaca gaccgccacc gtcgtggtgg taagggtgaa acggtgcggt 180
aagagcgcac cagcatcccg ggtgaccggg gtggctaggc aaaccccacc cgaagcaagg 240
ccaagaaggc cgcaccgaaa gtgcggccgc gcagacgttt gagggctgct cgcccgagtc 300
tgcgggtagg ccgctcgagg cacccggtaa cggtgtgtcc agatggatgg tcgtcgccgt 360
gccgccgtgg attaaagccg cggcggtggg gaacagaatc cggcttacag gccaact 417

<210> SEQ ID NO 30
<211> LENGTH: 425
<212> TYPE: DNA
<213> ORGANISM: Mycobacterium marinum

<400> SEQUENCE: 30
cggatgagtt ggctgggcgg ccgcggctcg ggttgggctc gtgttgtcac gagttcagcg 60
ccgaatcgag gaaagtccgg acttcacaga gctgggtgat tgctaacagc aatccgaggt 120
gactcgcggg aaagtgccac agaaaacaga ccgccaccct cgcggtggta agggtgaaac 180
ggtgcggtaa gagcgcacca gcaccccggg tgaccggggt ggctaggcaa accccacccg 240
aagcaaggtc aagaaggccg taccgtaggg tgcggccgcg caggcgtttg agggctgctc 300
gcccgagtct gcgggtaggc cgctcgaggt acccggcaac ggtgtgccca gatggatggt 360
cgccgccgcg ccgccgctgg ttcagccgcg gcggtgtgga acagaatccg gcttacgggc 420
caaca 425

<210> SEQ ID NO 31
<211> LENGTH: 399
<212> TYPE: DNA
<213> ORGANISM: Mycobacterium intracellulare

<400> SEQUENCE: 31
cggatgagtt ggctgggcgg ccgcgggccg tcgcaaggcg gttcgaggaa agtccggact 60
tcacagagca gggtgattgc taacggcaat ccgaggtgac tcgcgggaaa gtgccacaga 120
aaacagaccg ccaccctcgc ggtggtaagg gtgaaacggt gcggtaagag cgcaccagca 180
tcccgggtga ccggggtggc tcggcaaacc ccacccgaag caaggccaag aaggccgcac 240
cgctggtgcg gccgcgcagg cgttcgaggg ctgctcgccc gagcctgcgg gtaggccgct 300
cgaggcaccc ggtgacggtg tgtccagatg gatggtcgcc gccgcaccgc cgttgctcac 360
gcgcggcggt gtggaacaga atccggctta caggccaac 399

<210> SEQ ID NO 32
<211> LENGTH: 416
<212> TYPE: DNA
<213> ORGANISM: Mycobacterium gastri

<400> SEQUENCE: 32
cggatgagtt ggctgggcgg ccgcggctcg agtcggttcg caaggaccgg cgccgagtcg 60
aggaaagtcc ggacttcaca gagcagggtg attgctaacg gcaatccgag gtgactcgcg 120
ggaaagtgcc acagaaaaca aaccgccacc ctcgcggtgg taagggtgaa acggtgcggt 180
aagagcgcac cagcatcccg ggtgaccggg gtggctaggc aaaccccacc cgaagcaagg 240
ccaagaaggc cgcaccgaag gtgcggccgc gcagacgatc gagggttgct cgcccgagtc 300
tgcgggtagg ccgcttgagg cacccggtga cggtgtgtcc agatggatgg tcgccgccgt 360
gccgccgttg gttcagccgc ggcggcaggg aacagaatcc ggcttacagg ccaaca 416

<210> SEQ ID NO 33
<211> LENGTH: 416
<212> TYPE: DNA
<213> ORGANISM: Mycobacterium kansasii

<400> SEQUENCE: 33
cggatgagtt ggctgggcgg ccgcggctcg agttggttcg caaggatcgg cgccgagccg 60
aggaaagtcc ggacttcaca gagcagggtg attgctaacg gcaatccgag gtgactcgcg 120
ggaaagtgcc acagaaaaca aaccgccatc ctcgtggtgg taagggtgaa acggtgcggt 180
aagagcgcac cagcatcccg ggtgaccggg gtggctaggc aaaccccacc cgaagcaagg 240
ccaagaaggc cgcaccgaag gtgcggccgc gcagacgccg gagggttgct cgcccgagtc 300
tgcgggtagg ccgctcgagg cacccggtga cggtgtgtcc agatggatgg tcgccgccgt 360
gccgccgttg gttcagccgc ggcggcaggg aacagaatcc ggcttacagg ccaaca 416

<210> SEQ ID NO 34
<211> LENGTH: 427
<212> TYPE: DNA
<213> ORGANISM: Mycobacterium microti

<400> SEQUENCE: 34
cggatgagtt ggctgggcgg ccgcggctcg cgtagggctt gtgtggattc acgaggttca 60
gcgtcgagtc gaggaaagtc cggacttcac agagcagggt gattgctaac ggcaatccga 120
ggtgactcgc gggaaagtgc cacagaaaac agaccgccat cctcgtggtg gcaagggtga 180
aacggtgcgg taagagcgca ccagcattcc gggtgaccgg ggtggctagg caaaccccac 240
ccgaagcaag gccaagaagg ccgcaccgaa agtgcggccg cgcaggcgct tgagggttgc 300
tcgcccgagc ctgcgggtag gccgctcgag gcacccggta acggtgtgtc cagatggatg 360
gtcgccgccg tgccgccgtt agcttggctg tggcggcgcg gaacagaatc cggcttacag 420
gccaaca 427

<210> SEQ ID NO 35
<211> LENGTH: 427
<212> TYPE: DNA
<213> ORGANISM: Mycobacterium bovis

<400> SEQUENCE: 35
cggatgagtt ggctgggcgg ccgcggctcg cgtagggctt gtgtggattc acgaggttca 60
gcgtcgagtc gaggaaagtc cggacttcac agagcagggt gattgctaac ggcaatccga 120
ggtgactcgc gggaaagtgc cacagaaaac agaccgccat cctcgtggtg gcaagggtga 180
aacggtgcgg taagagcgca ccagcattcc gggtgaccgg ggtggctagg caaaccccac 240
ccgaagcaag gccaagaagg ccgcaccgaa agtgcggccg cgcaggcgct tgagggttgc 300
tcgcccgagc ctgcgggtag gccgctcgag gcacccggta acggtgtgtc cagatggatg 360
gtcgccgccg tgccgccgtt agcttggctg tggcggcgcg gaacagaatc cggcttacag 420
gccaaca 427

<210> SEQ ID NO 36
<211> LENGTH: 427
<212> TYPE: DNA
<213> ORGANISM: Mycobacterium tuberculosis

<400> SEQUENCE: 36
cggatgagtt ggctgggcgg ccgcggctcg cgtagggctt gtgtggattc acgaggttca 60
gcgtcgagtc gaggaaagtc cggacttcac agagcagggt gattgctaac ggcaatccga 120
ggtgactcgc gggaaagtgc cacagaaaac agaccgccat cctcgtggtg gcaagggtga 180
aacggtgcgg taagagcgca ccagcattcc gggtgaccgg ggtggctagg caaaccccac 240

-continued

```
ccgaagcaag gccaagaagg ccgcaccgaa agtgcggccg cgcaggcgct tgagggttgc    300

tcgcccgagc ctgcgggtag gccgctcgag gcacccggta acggtgtgtc cagatggatg    360

gtcgccgccg tgccgccgtt agcttggctg tggcggcgcg gaacagaatc cggcttacag    420

gccaact                                                              427
```

<210> SEQ ID NO 37
<211> LENGTH: 415
<212> TYPE: DNA
<213> ORGANISM: Mycobacterium gastri

<400> SEQUENCE: 37

```
cggatgagtt ggctgggcgg ccgcggctcg agtcggttcg caaggaccgg cgccgagtcg     60

aggaaagtcc ggacttcaca gagcagggtg attgctaacg gcaatccgag gtgactcgcg    120

ggaaagtgcc acagaaaaca aaccgccacc ctcgcggtgg taagggtgaa acggtgcggt    180

aagagcgcac cagcatcccg ggtgaccggg gtggctaggc aaaccccacc cgaagcaagg    240

ccaagaaggc cgcacgaagg tgcggccgcg cagacgatcg agggttgctc gcccgagtct    300

gcgggtaggc cgcttgaggc acccggtgac ggtgtgtcca gatggatggt cgccgccgtg    360

ccgccgttgg ttcagccgcg gcggcaggga acagaatccg gcttacaggc caaca         415
```

<210> SEQ ID NO 38
<211> LENGTH: 415
<212> TYPE: DNA
<213> ORGANISM: Mycobacterium kansasii

<400> SEQUENCE: 38

```
cggatgagtt ggctgggcgg ccgcggctcg ggttggttcg caaggatcgg cgccgagtcg     60

aggaaagtcc ggacttcaca gagcagggtg attgctaacg gcaatccgag gtaactcgcg    120

ggaaagtgcc acagaaaaca aaccgccatc ctcgtggcgg taagggtgaa acggtgcggt    180

aagagcgcac cagcatcccg ggtgaccggg gtggctaggc aaaccccacc cgaagcaagg    240

ccaagaaggc cgcaccaagg tgcggccgcg cagacgctcg agggttgctc gcccgagtct    300

gcgggtaggc cgcttgaggc acccggtgac ggtgtgtcca gatggatggt cgccgccgtg    360

ccgccgttgg ttcagccgcg gcggcaggga acagaatccg gcttacaggc caaca         415
```

<210> SEQ ID NO 39
<211> LENGTH: 415
<212> TYPE: DNA
<213> ORGANISM: Mycobacterium kansasii

<400> SEQUENCE: 39

```
cggatgagtt ggctgggcgg ccgcggctcg ggttggttcg caaggatcgg cgccgagtcg     60

aggaaagtcc ggacttcaca gagcagggtg attgctaacg gcaatccgag gtaactcgcg    120

ggaaagtgcc acagaaaaca aaccgccatc ctcgcggtgg taagggtgaa acggtgcggt    180

aagagcgcac cagcatcccg ggtgaccggg gtggctaggc aaaccccacc cgaagcaagg    240

ccaagaaggc cgcaccaagg tgcggccgcg cagacgctcg agggttgctc gcccgagtct    300

gcgggtaggc cgcttgaggc acccggtgac ggtgtgtcca gatggatggt cgccgccgtg    360

ccgccgttgg ttcagccgcg gcggcaggga acagaatccg gcttacaggc caaca         415
```

<210> SEQ ID NO 40
<211> LENGTH: 415
<212> TYPE: DNA
<213> ORGANISM: Mycobacterium kansasii -continued

<400> SEQUENCE: 40

```
cggatgagtt ggctgggcgg ccgcggctcg agttggttcg caaggatcgg cgccgagtcg     60
aggaaagtcc ggacttcaca gagcagggtg attgctaacg gcaatccgag gtaactcgcg    120
ggaaagtgcc acagaaaaca aaccgccatc ctcgcggtgg taagggtgaa acggtgcggt    180
aagagcgcac cagcatcccg ggtgaccggg gtggctaggc aaaccccacc cgaagcaagg    240
ccaagaaggc cgcaccaagg tgcggccgcg cagacgctcg agggttgctc gcccgagtct    300
gcgggtaggc cgcttgaggc acccggtgac ggtgtgtcca gatggatggt cgccgccgtg    360
ccgccgttgg ttcagccgcg gcggcaggga acagaatccg gcttacaggc caaca          415
```

<210> SEQ ID NO 41
<211> LENGTH: 415
<212> TYPE: DNA
<213> ORGANISM: Mycobacterium kansasii

<400> SEQUENCE: 41

```
cggatgagtt ggctgggcgg ccgcggctcg agttggttcg caaggatcgg cgccgagccg     60
aggaaagtcc ggacttcaca gagcagggtg attgctaacg gcaatccgag gtgactcgcg    120
ggaaagtgcc acagaaaaca aaccgccatc ctcgtggtgg taagggtgaa acggtgcggt    180
aagagcgcac cagcatcccg ggtgaccggg gtggctaggc aaaccccacc cgaagcaagg    240
ccaagaaggc cgcacgaagg tgcgggcggg cagacgccgg agggttgctc gcccgagtct    300
gcgggtaggc cgctcgaggc acccggtgac ggtgtgtcca gatggatggt cgccgccgtg    360
ccgccgttgg ttcagccgcg gcggcaggga acagaatccg gcttacaggc caaca          415
```

<210> SEQ ID NO 42
<211> LENGTH: 415
<212> TYPE: DNA
<213> ORGANISM: Mycobacterium kansasii

<400> SEQUENCE: 42

```
cggatgagtt ggctgggcgg ccgcggctcg agttggttcg caaggatcgg cgccgagtcg     60
aggaaagtcc ggacttcaca gagcagggtg attgctaacg gcaatccgag gtaactcgcg    120
ggaaagtgcc acagaaaaca aaccgccatc ctcgcggtgg taagggtgaa acggtgcggt    180
aagagcgcac cagcatcccg ggtgaccggg gtggctaggc aaaccccacc cgaagcaagg    240
ccaagaaggc cgcaccaagg tgcggccgcg cagacgctcg agggttgctc gcccgagtct    300
gcgggtaggc cgcttgaggc acccggtgac ggtgtgtcca gatggatggt cgccgccgtg    360
ccgccgttgg ttcagccgcg gcggcaggga acagaatccg gcttacaggc caaca          415
```

<210> SEQ ID NO 43
<211> LENGTH: 415
<212> TYPE: DNA
<213> ORGANISM: Mycobacterium kansasii

<400> SEQUENCE: 43

```
cggatgagtt ggctgggcgg ccgcggctcg agttggttcg caaggatcgg cgccgagccg     60
aggaaagtcc ggacttcaca gagcagggtg attgctaacg gcaatccgag gtgactcgcg    120
ggaaagtgcc acagaaaaca aaccgccatc ctcgtggtgg taagggtgaa acggtgcggt    180
aagagcgcac cagcatcccg ggtgaccggg gtggctaggc aaaccccacc cgaagcaagg    240
ccaagaaggc cgcacgaagg tgcggccgcg cagacgccgg agggttgctc gcccgagtct    300
gcgggtaggc cgctcgaggc acccggtgac ggtgtgtcca gatggatggt cgccgccgtg    360
```

-continued ccgccgttgg ttcagccgcg gcggcaggga acagaatccg gcttacaggc caaca 415

<210> SEQ ID NO 44
<211> LENGTH: 398
<212> TYPE: DNA
<213> ORGANISM: Chlamydia trachomatis

<400> SEQUENCE: 44
tcggaagagt aaggcaaccg ctgaaaccag ctttttaaaa aagatgagta ccagaggaaa 60
gtccggactt tataagaaaa gatgctggag aaattccagg ggccgtaagg ctacggaaag 120
tgcaacagaa aacactccgc tataaattgt ataatttata gacaggctga aaaatcttac 180
tttaggagta agagctgcta gggagaccta gcagacttgt aaaccccatc tgaagcaaga 240
gaaaaagtta tttgtttctg caaacaacct ttctaacgaa aggcacaggc tttttcataa 300
tcgcttgagg agtacagtaa tgtgctccct agatgaatgg ttgcccgcaa gcaagaactt 360
ccgttcgtgc ttgtcgacag aayccggctt actcgctc 398

<210> SEQ ID NO 45
<211> LENGTH: 394
<212> TYPE: DNA
<213> ORGANISM: Chlamydia suis

<400> SEQUENCE: 45
tcggaagagt aaggcagccg ctggagcagt ttgtttaaag ctgatgtcag aggaaagtcc 60
ggacttcata agaaaagatg ctggagaaat tccaggggcc gagaggctac ggaaagtgca 120
acagaaaaca ctccgctata aattgcaaaa tttatagaca ggctgaaaaa tcctacttta 180
agagtaggag ctgctgggga gacccggtag acctgtaaac cccatctgaa gcaagagaaa 240
aagtcttttg tctctgcaaa gaacctctct aagggaaggt tcagactttt tcataatcgc 300
ttgagaagta tagtaatgtg cttcctagat gaatggctgc ccgcaagcag gaatttttat 360
tcgcgcttgt tgacagaayc cggcttactc gctc 394

<210> SEQ ID NO 46
<211> LENGTH: 395
<212> TYPE: DNA
<213> ORGANISM: Chlamydia muridarum

<400> SEQUENCE: 46
tcggaagagt aaggcaaccg ctgagccagt tttagaaaaa ctgcgtatca gaggaaagtc 60
cggacttcgt aagaaaagat gctggagaaa ttccaggggc cgtaaggcta cggaaagtgc 120
aacagaaaac attccgctat aaatgatatc atttatagac aggctgaaaa atcctacttt 180
aggagtagga gctgctaggg agacctggta gacttgtaaa ccccatctga agcaagagaa 240
aaagttattt gtctctgcaa aatcctttct aatgaaaggc ataaactttt tcataatcgc 300
ttgaggagta cagtaatgtg ctccctagat gaatggttgc ccacaagtaa gaatttctta 360
ttcgtacttg ttgacagaay ccggcttact cgctc 395

<210> SEQ ID NO 47
<211> LENGTH: 399
<212> TYPE: DNA
<213> ORGANISM: Chlamydia pecorum

<400> SEQUENCE: 47
tcggaagagt aaggcaaccg ctgtttatgc tttttcacaa tgaaaaagca taaagagagg 60
aaagtctgga cttcataaga aaagatactg gagaaactcc aggggccgtg aggctacgga 120
aagtgcaaca gaaaacattc cgctataaaa tgaaagtttt atagacaggc tgaaaattcc 180
tactttagga gtaggagcta ttaaggtgac ttaatagaca tgcaaaccct atctgaagca 240
agagaaaaaa gctttttgt ttctgcaaaa ttgagaagtt ttcttctcat aagtttttc 300 ataatcgctc gagggattta gagatagatc ccctagatga atggttgccc tcagggagac 360
gtttgtccac cctgcagaca gaayccggct tactcgctc 399

<210> SEQ ID NO 48
<211> LENGTH: 388
<212> TYPE: DNA
<213> ORGANISM: Chlamydia caviae

<400> SEQUENCE: 48
tcggaagagt aaggcaaccg ctttttatat ctctagttag gtatactgag aggaaagtct 60
ggacttcata agaagagata ctggagaaac tccaggggcc gtaaggctac ggaaagtgca 120
acagaaaaca ctccgctata aaagggtctt tttatagaca ggctgaaaat tcctacttta 180
agagtaggag ctattaaggt gacttaatag acatgcaaac cctatctgaa gcaagagaaa 240
aagtttttgt ttctgcatag tgagggatag tattcctcat aaactttttc ataatcgctt 300
gaggggtata gtaatatgcc ccctagatga atggttgccc tcaagatggt cttttccatc 360
ttgtagacag aayccggctt actcgctc 388

<210> SEQ ID NO 49
<211> LENGTH: 376
<212> TYPE: DNA
<213> ORGANISM: Chlamydia felis

<400> SEQUENCE: 49
tcggaagagt aaggcaaccg cttcctgtat ctctagtaga tatggtaaga ggaaagtctg 60
gacttcataa gaagagatac tggagaaact ccaggggccg taaggctacg gaaagtgcaa 120
cagaaaacac tccgctataa tatagacagg ctgaaaattc ctactttaag agtaggagct 180
attaaggtga cttaatagac gtgcaaaccc tatctgaagc aagagaaaaa gtttttgttt 240
ctgcataatg aggagctctg ttcctcataa actttttcac aatcgcttga gggatatagt 300
aatatatccc ctagatgaat ggttgccctc aagatggtct ttgccatctt gtagacagaa 360
yccggcttac tcgctc 376

<210> SEQ ID NO 50
<211> LENGTH: 388
<212> TYPE: DNA
<213> ORGANISM: Chlamydia psittaci

<400> SEQUENCE: 50
tcggaagagt aaggcaaccg ctttttgtac ctttactaag gtatattaag aggaaagtct 60
ggacttcata agaaaagata ctggagaaac tccaggggcc gtaaggctac ggaaagtgca 120
acagaaaaca ttccgctata aaagggtctt tttatagaca ggctgaaaat tcctatttta 180
agaataggag ctattaaggt gacttagtag acgtgcaaac cctatctgaa gcaagagaaa 240
aagtttttgt ttctgcataa tgaggaatgg tattcctcat gaactttttc ataatcgctt 300
gagggatata gtaatatatc ccctagatga atggttgccc tcaagatggg ttttctcatc 360
ttgtagacag aayccggctt actcgctc 388

<210> SEQ ID NO 51
<211> LENGTH: 390
<212> TYPE: DNA

-continued

<213> ORGANISM: Chlamydia abortus

<400> SEQUENCE: 51

```
tcggaagagt aaggcaaccg ctttttgtac cttaactaag gtagattaag aggaaagtct     60

ggacttcata agaaaagata ctggagaaac tccaggggcc gtaaggctac ggaaagtgca    120

acagaaaaca ttccgctata aaagggtctt tttatagaca ggctgaaaat tcctatttta    180

agaataggag ctattaaggt gacttagtag acatgcaaac cctatctgaa gcaagagaaa    240

aagtttttgt ttctgcataa tgagagggag ggtatccctc atgaactttt tcataatcgc    300

ttgagggata tagtaatata tcccctagat gaatggttgc cctcaagatg agttttttca    360

tcttgtagac agaayccggc ttactcgctc                                     390
```

<210> SEQ ID NO 52
<211> LENGTH: 392
<212> TYPE: DNA
<213> ORGANISM: Chlamydia pneumoniae

<400> SEQUENCE: 52

```
tcggaagagt aaggcaaccg ctgtttatat ttctcaaaaa atataaagag aggaaagtct     60

ggacttcata agagaagata ctggagaaat tccaggggcc gtaaggctac ggaaagtgca    120

acagaaaaca ctccgctata aaatttattt tatagacagg ctgaaaattc ctactttagg    180

agtaggagcc attaaggtga cttaataggc atgcaaaccc tatctgaagc aagagaaaaa    240

agctttttgt gtctgcaaat gtgagaggaa ttcctcccat aggctttttc gaaatcgctt    300

gagggatcta gtaatagctc ccctagatga atggttgccc ttaggatagt tcgcaagagc    360

tatcttatag acagaayccg gcttactcgc tc                                  392
```

<210> SEQ ID NO 53
<211> LENGTH: 313
<212> TYPE: DNA
<213> ORGANISM: Parachlamydia acanthamoebae

<400> SEQUENCE: 53

```
rrmgrrgagg aaagtccgga ctttatagga gaggatgcca gtgaaagact gggggccgca     60

aggctacgga aagtgccaca gaaaacaaac cgctaacaag ctatgcttgt tagatagggt    120

gaaatgcctg ctttaggagc atggccttat ctagagaaat ttagaaagtg gtaaacccca    180

tctcaagcaa gacggaaata aagcgataca gttctccgct gtgctttaga aaagtcgctt    240

gagggtttcg gtgacggcgc ccctagagga atgattgctc gtctgctttg cagaccgaca    300

gaacccggct tay                                                       313
```

<210> SEQ ID NO 54
<211> LENGTH: 299
<212> TYPE: DNA
<213> ORGANISM: Simkania negevensis

<400> SEQUENCE: 54

```
rrmgrrgagg aaagtccgga cttcgcagaa aaaggtgcca gtgaaaaact gggggccgta     60

aggctacgga aagtgtaaca gaaaacaaac cgctaattct acctaggtaa gattagacag    120

gatgaaaatg tcgagcttat ggctcgacct ctttgtggaa acacaaggac gctgcaaacc    180

ccatctgaag caagaaagag ttcgtttcag tttttcgctc aggaactctt agagtcgctc    240

gaggattttg gtgacaaagt ccctagatga atgattgcct cgcacagaac ccggcttay     299
```